(12) United States Patent
Flanner et al.

(10) Patent No.: US 9,125,803 B2
(45) Date of Patent: Sep. 8, 2015

(54) GASTRIC RELEASE PULSE SYSTEM FOR DRUG DELIVERY

(75) Inventors: Henry H. Flanner, Montgomery Village, MD (US); Donald Treacy, Woodbine, MD (US); Sanna Tolle-Sander, North Potomac, MD (US); Scott Ibrahim, Owings Mills, MD (US); Marcus Schestopol, Washington, DC (US); Beth A. Burnside, Bethesda, MD (US)

(73) Assignee: Shionogi Inc., Florham Park, NJ (US)

( * ) Notice: Subject to any disclaimer, the term of this patent is extended or adjusted under 35 U.S.C. 154(b) by 1440 days.

(21) Appl. No.: 11/644,707

(22) Filed: Dec. 22, 2006

(65) Prior Publication Data
US 2007/0154547 A1 Jul. 5, 2007

Related U.S. Application Data

(60) Provisional application No. 60/755,043, filed on Dec. 30, 2005.

(51) Int. Cl.
| A61K 9/22 | (2006.01) |
| A61K 9/00 | (2006.01) |
| A61K 9/16 | (2006.01) |
| A61K 9/20 | (2006.01) |
| A61K 9/24 | (2006.01) |
| A61K 9/50 | (2006.01) |

(52) U.S. Cl.
CPC .............. *A61K 9/0004* (2013.01); *A61K 9/0065* (2013.01); *A61K 9/1623* (2013.01); *A61K 9/1635* (2013.01); *A61K 9/1652* (2013.01); *A61K 9/209* (2013.01); *A61K 9/2027* (2013.01); *A61K 9/2054* (2013.01); *A61K 9/2077* (2013.01); *A61K 9/2081* (2013.01); *A61K 9/2086* (2013.01); *A61K 9/501* (2013.01); *A61K 9/5015* (2013.01); *A61K 9/5026* (2013.01); *A61K 9/5042* (2013.01); *A61K 9/5073* (2013.01); *A61K 9/5084* (2013.01)

(58) Field of Classification Search
CPC . A61K 9/0004; A61K 9/5084; A61K 9/1623; A61K 9/1652; A61K 9/1635; A61K 9/2027; A61K 9/2054; A61K 9/2077; A61K 9/2081; A61K 9/2086; A61K 9/209; A61K 9/501; A61K 9/5015; A61K 9/5026; A61K 9/5042; A61K 9/5073; A61K 9/0065

See application file for complete search history.

(56) References Cited

U.S. PATENT DOCUMENTS

| 4,674,808 | A | 6/1987 | Phy et al. |
| 5,007,790 | A | 4/1991 | Shell et al. |
| 6,476,006 | B2 * | 11/2002 | Flashner-Barak et al. ...... 514/76 |
| 6,544,555 | B2 | 4/2003 | Rudnic et al. |
| 6,635,280 | B2 | 10/2003 | Shell et al. |
| 6,669,948 | B2 | 12/2003 | Rudnic et al. |
| 6,682,759 | B2 | 1/2004 | Lim et al. |
| 6,723,341 | B2 | 4/2004 | Rudnic et al. |
| 2001/0055613 | A1 | 12/2001 | Burnside et al. |
| 2003/0077323 | A1 * | 4/2003 | Rudnic et al. ................. 424/468 |
| 2004/0121010 | A1 * | 6/2004 | Hirsh et al. .................... 424/468 |
| 2005/0019401 | A1 * | 1/2005 | Burnside et al. .............. 424/468 |
| 2005/0163842 | A1 | 7/2005 | Boehm et al. |

FOREIGN PATENT DOCUMENTS

WO       WO 03/051304      *   6/2003

OTHER PUBLICATIONS

Chawla, Garima et al., Pharmacetuical Technology, Jul. 2003, pp. 50-68.*
ADCO-Acylovir, Pharmaceutical Industry, Apr. 2004, pp. 1-3.*

* cited by examiner

Primary Examiner — Anoop Singh
Assistant Examiner — Doan Phan
(74) Attorney, Agent, or Firm — MH2 Technology Law Group, LLP

(57) ABSTRACT

Disclosed are pharmaceutical products for providing pulses of at least one pharmaceutically active ingredient from a patient's stomach, or from a subsequent gastrointestinal site proximal thereto, for absorption thereof at a site(s) more distal in the gastrointestinal tract than the patient's stomach, or than the subsequent gastrointestinal site proximal thereto. The product comprises first, second, and third pharmaceutical dosage forms, each of which comprises at least one pharmaceutically active agent and a pharmaceutically acceptable carrier. The product is formulated such that at least two of the first, second, and third pharmaceutical dosage forms further comprise means for providing temporary gastric-retention of the at least two of the first, second, and third pharmaceutical dosage forms within the patient's stomach, or at the subsequent gastrointestinal site proximal thereto.

9 Claims, 9 Drawing Sheets

GASTRIC RELEASE PULSE SYSTEM FOR DRUG DELIVERY

This application claims priority to U.S. Provisional Application Ser. No. 60/755,043 filed Dec. 30, 2005, the disclosures of which are hereby incorporated by reference in their entireties.

This invention is directed to a pharmaceutical product useful for providing pulses of pharmaceutically active ingredients from a patient's stomach, or from a subsequent gastrointestinal site proximal to a patient's stomach, for absorption at a site more distal in the gastrointestinal tract than the patient's stomach, or at a site more distal in the gastrointestinal tract than the subsequent gastrointestinal site proximal to the patient's stomach.

As used herein the term "patient" shall denote any human or mammal to whom the hereinabove described or hereinbelow described products are administered, and/or upon whom the hereinabove described or hereinbelow described methods are practiced. So defined, the term "patient" shall include any such human or mammal, without regard to whether the administration of the products, and/or the practice of the methods, occurs while such human or mammal is or is not under the care, control, or observation of any physician, clinician, veterinarian, husbandman, parent, guardian, or like custodian; without regard to whether the administration of the products, and/or the practice of the methods, occurs while such human or mammal is or is not a subject participating in, or being subjected to, any study or research program; without regard to whether the products are self-administered, and/or the methods are self-practiced, by such human or mammal; and without regard to whether the administration of the products, and/or the practice of the methods, occurs by way of some inanimate means.

In a first aspect, the product comprises at least three pharmaceutical dosage forms, each of which comprises at least one pharmaceutically active agent and a pharmaceutically acceptable carrier. In a second aspect at least two of the at least three pharmaceutical dosage forms of the product each further comprise a means for providing temporary gastric-retention of these two pharmaceutical dosage forms within the patient's stomach, or at a subsequent gastrointestinal site proximal to the patients' stomach.

In one embodiment all three of the at least three pharmaceutical dosage forms further comprise a means for providing temporary gastric-retention of the three pharmaceutical dosage forms within the patient's stomach, or at a subsequent gastrointestinal site proximal to the patients' stomach.

There is a need in the pharmaceutical formulation arts for improved pulsatile delivery of active ingredients, such as can provide faster rising PK plasma profiles, higher Cmax's and more (longer) separation between multiple Cmax's. The current pulsatile art is based on pH-dependent polymers, and osmotic systems and other similarly pH-independent systems, to provide pulsatile delivery. None of these systems, however, provide sufficiently rapid and adequately separated pulses.

Several drug therapies may benefit by extended pulsatile dosing, such as therapies relating to the use of anti-infective agents (e.g., antibiotics, antivirals, anti-fungal agents, and antineoplastic agents). In some embodiments the instant invention may be practiced to enhance and optimize features of PULSYS™, a preferably oral drug delivery technology that enables once-daily pulsatile dosing, as that technology is disclosed and embodied in U.S. Pat. No. 6,544,555; U.S. Pat. No. 7,025,989; U.S. Pat. No. 6,541,014; U.S. Pat. No. 7,074,417; U.S. patent application Publication 20030099707; U.S. patent application Publication 20030147953; U.S. Pat. No. 7,108,859; and U.S. Pat. No. 7,105,174 the disclosures of which are hereby incorporated by reference in their entireties. Like the Pulsys™ technology, the delivery system of the instant invention, in some embodiments, provides distinctly discernible pharmacokinetic curves at specific points in time for each of the delivered pulses of active ingredient.

The hereinabove described and hereinbelow described products and methods may also be particularly useful in chronotherapeutic regimens, wherein a patient's medical treatments are coordinated with his/her biological rhythms. Chronotherapy, as may be benefited by the instant invention, may prove particularly useful in the administration of anti-hypertension drugs. For example Sica et al. have suggested that optimizing the dosing regimens of beta blockers such that their peak anti-hypertensive effects are realized in the hours around waking (when coronary risks are greatest) may improve the drugs' abilities to reduce coronary events. Sica et al. also noted that current beta blocker formulations and regimens are sub-optimally dosed, usually once daily in the morning, whereby the lowest plasma levels and the smallest anti-hypertensive effects occur during the morning hours, when risk of cardiac events is greatest. (See Sica D., Neutel J., Weber M., Manowitz N.; *The Antihypertensive Efficacy and Safety of a Chronotherapeutic Formulation of Propanolol in Patients with Hypertension*; Journal of Clinical Hypertension 6(5):231-241, 2004. Other drug therapies that may benefit from the hereinabove described and hereinbelow described products and methods are those that work on a rising dose principle, such as drugs used to treat ADD or ADHD.

In addition to requiring better pulsatile delivery mechanisms there is also a need in the art for oral delivery methodologies that will extend the time available for absorption of an active ingredient that exhibits a limited window of absorption. The current art focuses on gastric retention, and continuous and/or sustained release delivery from swellable dosage forms. However, as contemplated by the current inventors a series of pulses of biologically active agent(s) that originate from the stomach for absorption later in the GI tract would provide the same extended window of absorption and the same prolonged release effects, with the added benefit that the release profile may be easily and infinitely tailored by comprising the dosage form of multiple pulses that can be arranged in the most beneficial pulse ratios, pulse release order, and pulse release rate.

For the conventional pulsatile systems of the prior art, microparticulate or multiparticulate core pellets and tablets coated with pH-dependent polymers are the most common types of pulsatile system. However, pH-dependent multiparticulate or microparticulate systems suffer from a spreading effect as these particles leave the stomach, see FIG. 1. This spreading of the multi- or micro-particles increases as the distance transited through the small intestine increases as illustrated in FIG. 1 A. Since pH-dependent compounds must pass a certain point in the GI tract where the pH is high enough to dissolve the pH-dependent coating, spreading out of the population of particles leads to a decrease in the in vivo release rate of the active agent as illustrated in FIG. 1 B. This is because at any given time only a certain portion of the particle population has passed the pH window where release occurs. So, if the spreading causes the population to take 2 hours or more to pass the window then the corresponding release rate must be at least 2 hours. In other words, while each particle releases quickly when it passes the pH trigger, the overall rate of release is diminished due to the spread of the pellets, and hence a decreased in vivo release rate. This release rate is not sufficient in many cases and leads to a phenomena known as "pulse collapse" where multiple pulses blend into one another and are not distinct, as seen in FIG. 2. The current invention overcomes this drawback of the prior art by eliminating pellet spread and the resultant "pulse collapse" in cases where distinct pulsing is required or beneficial, see FIGS. 3 and 4.

Prior art tablets coated with pH-dependent systems can overcome the spreading effect that dampens the apparent release rate in vivo. Typically for a multiple pulse system multiple tablets coated with polymers that dissolve at different pHs are manufactured and then one or more of the tablets is placed into a capsule to give a unitary multipulse system, as described in U.S. Pat. No. 5,229,131. One drawback with this approach is that tablet transit is generally faster than pellet transit, so the separation between pulses can be reduced by transit effects after gastric emptying. Another more problematic drawback is that the tablets may not exit the pylorus at the same time or in the proper order. Either of these phenomena can lead to the observation of "pulse collapse" as seen in microparticulate systems. The current invention overcomes these drawbacks by providing a mechanism for releasing multiple individual pulses from the stomach and in a time-controlled fashion rather than a pH-dependent or distance-controlled fashion. These pulses are not dependent on environment, thus even if the dosage form escapes or is ejected from the stomach, the time controlled release mechanism would still prevail.

Osmotic systems can provide adequate spacing between pulses, but suffer from slow release rates that often exhibit a further decline after a certain amount of active agent and/or osmotic agent has been released due to the nature of their delivery mechanism. Furthermore, it is not readily possible to accommodate more than three pulses or very large doses in a single osmotic dosage unit. These systems are acceptable in cases where the active ingredient has a very long absorption window and where release can occur over 2-6 hours or more. However, osmotic systems are also not suitable for cases where the pulsatile dose must be delivered in less than 2 hours. Also, most osmotic systems are provided in a tablet form, and so are not acceptable for administration to patients with difficulty swallowing, such as the very young or the elderly.

Other systems include the so-called pH-independent systems consisting of: osmotic bursting tablet or pellet systems, and other rupturing or eroding systems of tablets or pellets. These systems can also suffer from pellet spread and other GI transit effects similar to pH-dependent systems. More importantly, these systems are not suitable for absorption window limited compounds, because they can transit out of the absorbing region of the GI tract before releasing their contents. The current invention would overcome these drawbacks by combining these pH-independent systems with gastric retentive technologies that would allow the devices to remain above or within the window of absorption. The resulting improved pharmacokinetic profile of the current invention can be simulated computationally, or otherwise, and be compared with the prior art, as seen in FIGS. 3 and 4.

Furthermore, compounds with a small window of absorption (i.e. compounds that are absorption window limited because of low permeability, low solubility, or other factors that limit absorption to the small intestine) lose pulse bioavailability and pulse definition if drug release occurs too late within, or after, the window of absorption. For pH-dependent systems the effect is usually seen with enteric polymers that dissolve above about pH 6-6.5, as the product in FIG. 2. For another example of poor absorption of late pulses also see FIGS. 4a and 4b in U.S. Pat. No. 4,250,166.

To overcome the problems presented by the small window of absorption of some active ingredients the art in recent years has developed the concept of gastric retention, as is discussed in the review by G. Chawla et al., "Gastroretention A Means to Address Regional Variability in Intestinal Drug Absorption," *Pharmaceutical Technology*, July 2003, and in the review by Hou et al, "Gastric Retentive Dosage Forms: A Review," *Critical Reviews™ in Therapeutic Drug Carrier Systems*, June, 2003, the disclosures of each of which are hereby incorporated herein by reference in their entireties. This retention in the stomach is achieved by use of bioadhesive ingredients or by size exclusion phenomena from highly swellable dosage forms, particularly tablets. However, gastric retention has previously been limited to sustained-release or two-pulse systems where the first pulse usually provides immediate release and the second pulse provides sustained release, see for example U.S. Pat. No. 5,007,790; U.S. Pat. No. 6,635,280; U.S. Pat. No. 6,797,283; and U.S. Pat. No. 6,682,759. Generally, gastro-retentive devices of the prior art, whether bioadhesive or size limited, do not exhibit release rates rapid enough to achieve the desired pulsatility of the present invention. Nor do they contemplate the use of 3 or more pulses to effect a sustained release mimetic profile.

BRIEF SUMMARY OF THE INVENTION

The current invention is directed to a novel gastric-retentive and/or upper enteric-retentive product, whereby dosage forms release multiple pulses in the stomach or upper GI tract for absorption in a later part of the GI tract in order to improve the pharmacokinetic profile of the pulses over the prior art. The improved pharmacokinetic profile may be improved in its rate of absorption or in its bioavailability as compared to a conventional pulsatile dosage form. Different ways to measure improvement exist and may be characterized by AUC, Cmax, Tmax, partial AUC to Tmax, wagner-nelson fraction absorbed, or other modeled parameter(s) to measure absorption or absorption rate, such as those that can be achieved by developing an IVIVC; by using Gastro Plus™; or by use of a pulsatility index equation of the form $PI_n = Pulse_n Cmax/Pulse_n dose$, where n is the integer of the pulse in the dosage form, where higher numbers of n are related to later initiation of release, and where for the current invention all $PI_n$ are roughly equivalent in comparison to prior art technologies where the $PI_n$ decreases with increasing n, or where $PI_n$ of the current invention are substantially improved over a similar non-retentive pulse formulation $PI_n$. One of ordinary skill in the art will appreciate that except for the most extremely absorption window limited compounds, a low value for n, such as 1 or 2, will not show much improvement over a conventional dosage form; however a higher value for n will show improvement. The improved absorption and/or absorption rate is made possible by the location of release (i.e. within or above the absorption window such as the stomach or proximal small intestine) and the release mechanism of the dosage form (i.e. pH-independent).

In the case of increasing pulse distinction, this is achieved by rapidly releasing the pulses with improved separation in comparison to the prior art. Means to characterize this improvement could be quantified by use of a pulse separation index $PT_i$, where $PT_i = PT_n - PT_{n-1}$ where $PT_i$ is the time between any two pulses n and n−1 calculated by subtracting the $T_{max}$ of the earlier, or lower n, pulse from the later, or higher n, pulse. The $PT_i$ for a conventional dosage form would be calculated and compared to the $PT_i$ of a dosage form of the current invention with the expected result of a high value of $PT_i$ for the current invention in relation to the prior art.

The current invention is also anticipated to lead to improvements in pulse collapse, (i.e. a reduction in the pulse collapse by increasing the time to initiation of pulses). This might best be characterized by examining the lag time differential between pulses of the prior art and pulses of the current invention. To calculate a lag time differential an equation of the form $PL_i=PL_n-PL_{n-1}$ might be used, where $PL_i$ is the lag time differential between any two pulses. $PL_i$ is calculated by subtracting the lag time of an earlier pulse $PL_{n-1}$ from the lag time of a later pulse $PL_n$. When this calculation is made for prior art dosage forms the value of $PL_i$ will be lower in comparison to dosage forms of the current invention.

By releasing pulses from the stomach or upper GI tract the entire absorption window is now available for absorption window limited compounds, thus improving the pulsatility and bioavailability of absorption window limited compounds. Another advantage of the invention is that multiple pulses may be released from the stomach, thus providing an opportunity for the skilled pharmaceutical scientist to build the desired "composite" pharmacokinetic profile from many individual pulsatile components. The benefit of unlimited combinations of release rates, pulse ratios, and pulse ordering or lag time being available to the pharmaceutical formulator will be immediately appreciated by one of ordinary skill in the art. It can be envisioned by one skilled in the art that this could lead to multiple modified release profiles, including pulsatile profiles, sustained release profiles, and any necessary multiphasic release rate required to achieve clinical pharmacokinetic goals—such profiles not being attainable in the prior art, and especially not for those active agents having a limited window of absorption.

As used herein, and as is generally known in the art, a pharmaceutically active agent described as having a "limited window of absorption" or described as being "absorption window limited" means that the pharmaceutically active agent is one that is essentially only absorbed in the small intestine. More particularly, as is further known in the art, most dosage forms, whether as tablets, pellets, capsules, or solutions, take about 3 to 4 hours to traverse the small intestine (G. Chawla et al., "Gastroretention A Means to Address Regional Variability in Intestinal Drug Absorption," *Pharmaceutical Technology*, July 2003), whereby a pharmaceutically active agent having a limited window of absorption may be absorbed only during a period of 3 to 4 hours or less following the emptying of the pharmaceutically active agent from the stomach. This transit property prevents adequate delivery of pulses after 3 to 4 hours for such absorption window limited compounds. Furthermore, for many compounds the absorption rate decreases with distance and time down the GI tract, whereby the absorption rate and extent within the GI tract is such: duodenum>jejunum>ileum>>>colon or stomach. It will be recognized by those skilled in the art that the high bioavailability provided by the current invention is especially important for antibiotic products, since poor bioavailability results in high amounts of unabsorbed drug transiting into the colon where the microflora are adversely affected resulting in high incidences of side effects such as loose stools; vomiting; stomach upset; and in the most severe cases toxic megacolon, as can result from an overgrowth of *clostridium difficile* and other colonic microflora.

As one skilled in the art will realize the current invention is not only beneficial to absorption window limited compounds, but also to compounds with good absorption. This is because releasing pulses from the stomach or upper GI tract prevents the "spreading" of microparticulates through the GI tract and the resultant "pulse collapse" that can be seen even for compounds with good absorption properties. Thus, a pulsatile profile can have a more defined pulsatile shape, resulting in better disease treatment in some cases. Alternatively, a pulsatile profile of the current invention may exhibit a "rising dose" profile for a longer period of time than could be achieved by the prior art, which is beneficial to some disease states. Furthermore, a more well defined pulsatile profile may result in lower amounts of active agent, required to maintain the active agent within the therapeutic window, or it may maintain the active agent within the therapeutic window longer for a given dose as a direct result of the enhanced absorption provided by pulsing from the stomach.

In one aspect of the invention, retention in the stomach or upper GI tract is achieved by bioadhesive layers and/or dosage form size, such methods being known to one skilled in the art, as reviewed in each of G. Chawla et al., "Gastroretention A Means to Address Regional Variability in Intestinal Drug Absorption," *Pharmaceutical Technology*, July 2003; Hou et al, "Gastric Retentive Dosage Forms: A Review," *Critical Reviews™ in Therapeutic Drug Carrier Systems*, June, 2003; and Gothoskar, A V, Joshi, A M and Joshi "Pulsatile Drug Delivery Systems: A Review", NH, *Drug Delivery Technology*, June 2004 Vol. 4 Number 5; the disclosures of each of which are hereby incorporated herein by reference in their entireties. Accordingly, the retentive methods above also assist in the improved separation of pulses and improved absorption rates not contemplated by the prior art.

In a further aspect of the invention, rapid pulsatile release and improved separation of pulses is achieved by pH-independent or pH-dependent means known to those skilled in the art, non-limiting examples of which were reviewed in "A Review of Pulsatile Drug Delivery" by Bussemer and Bodmeier in the Winter 2001 issue of American Pharmaceutical Review, the disclosures of which are hereby incorporated herein by reference in their entireties.

In one aspect of the invention, the product operates by releasing multiple pulses from within the confines of the stomach, for absorption primarily in the duodenum. In another aspect the product operates by releasing multiple pulses from the stomach for absorption in the duodenum and jejunum. In still another aspect of the invention the product operates by releasing multiple pulses from the stomach for absorption primarily or substantially in the small intestine. In yet another aspect of the invention the product operates by releasing multiple pulses from the stomach for absorption in the small intestine and colon. In a further aspect the product operates by releasing multiple pulses from the stomach or the duodenum for absorption in the jejunum and/or ileum and/or colon. In yet another aspect of the invention the product operates by releasing multiple pulses from the duodenum or jejunum for absorption in the ileum or colon.

In a further aspect, this invention provides an orally administered product for pulsatile drug delivery, whereby at least three or more pulses are released from the stomach or proximal portion of the small intestine for absorption in a more distal part of the GI tract. In one aspect, all of the at least three pulses release from the stomach. In another aspect, at least one of the three or more pulses releases from the stomach and the other pulses release from the upper or proximal small intestine.

In another aspect, the pulsatile dosage form can be in the form of tablets, capsules, or in a sprinkle form such as beads or pellets contained in a capsule, pouch, or sachet. As used herein the terms "beads" or "pellets" shall include the art common terms "microparticulates" or "multiparticulates." The tablets of the invention may be multilayer in design or consist of different beads compressed into a tablet, or may be an osmotic multipulse design with sufficiently rapid release of each pulse.

In another aspect of one embodiment, the dosage form releases the at least three pulses separated by about at least one hour and each pulse is about at least 50% dissolved before release is initiated from the following pulse. In one aspect the pulses are released so that the corresponding Cmax and Tmax of each of the at least three pulses is distinguishable in a pharmacokinetic plasma profile. In another aspect the at least three pulses provide a pharmacokinetic plasma profile characteristically generated by a controlled or sustained release dosage form, however, the release of each pulse initiates at a different time or a different rate thusly creating such a profile.

In a further aspect, the invention comprises a method of treating a patient in need of a pharmaceutically active ingredient, which comprises administering the needed pharmaceutically active ingredient to the patient by way of the hereinabove described and hereinbelow described product, whereby the dosage form(s) is/are retained in the stomach, or in the upper intestine, for a period of time long enough for at least 2 of the at least 3 pulses to be released. The product may be administered in the fed state to take advantage of the interdigestive myoelectric motor complex or IMMC phases that effect gastric emptying and GI transit. The dosage form(s) may also contain a bioadhesive agent to supply the necessary retentive properties independent of the presence of food in the subject.

In a preferred embodiment, the invention comprises a method of treating a patient in need of anti-infective therapy which comprises administering the needed anti-infective to the patient by way of the hereinabove described and hereinbelow described product, whereby the dosage form(s) is/are retained in the stomach, or in the upper intestine, for a period of time long enough for at least 2 of the at least 3 pulses to be released. The product may be administered in the fed state to take advantage of the interdigestive myoelectric motor complex or IMMC phases that effect gastric emptying and GI transit. The dosage form(s) may also contain a bioadhesive agent to supply the necessary retentive properties independent of the presence of food in the subject.

BRIEF DESCRIPTION OF THE SEVERAL VIEWS OF THE DRAWINGS

FIG. 7(A) shows a core 40, containing a hydrophilic bioadhesive agent 13, and/or a hydrophobic bioadhesive agent 14, dispersed with drug in a matrix. FIG. 7(B) shows a core 50, containing drug and a hydrophilic bioadhesive agent 16 in a matrix coated with a hydrophobic bioadhesive agent 15.

DETAILED DESCRIPTION OF THE INVENTION

Figure 1A:
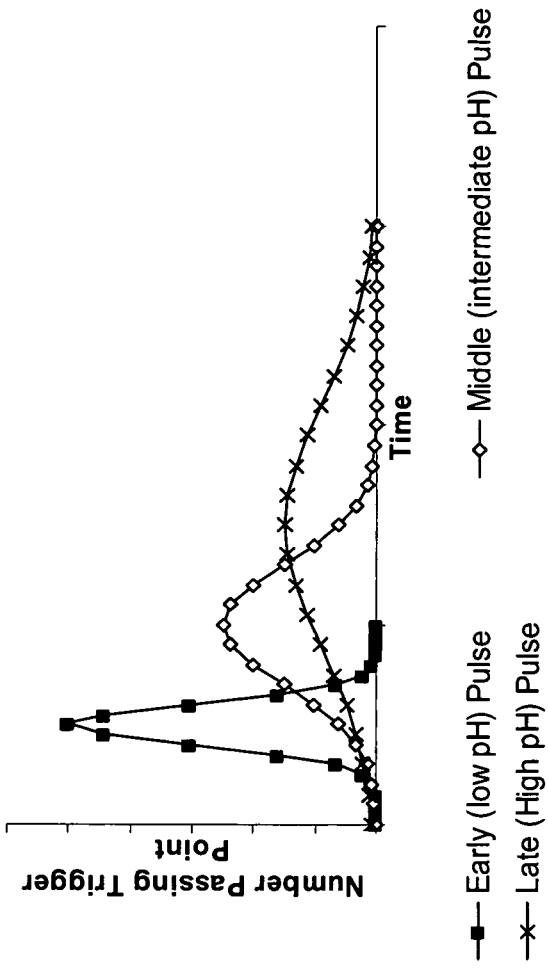
FIG. 1(A) shows the hypothetical number distribution of pH-dependant pellets passing their respective early middle and late trigger points. As the pH trigger point becomes higher and thus later in GI transit time the pellet population is subject to more spread, resulting in fewer pellets passing the trigger point per unit time thus prolonging the in vivo release rate as illustrated in FIG. 1(B).

The invention described in this application is directed to improving the pharmacokinetic profile attainable from modified release dosage forms of both absorption window limited and well absorbed compounds by releasing multiple "pulses," where the pulses are of the form of immediate and modified release dosage forms, from the stomach for substantial absorption in a more distal region of the GI tract by means of gastric retention. "Modified release" for the purposes of this application, encompasses various dosage form embodiments designed to modify the release of the active agent to make it other than simple immediate release, although immediate release may be one component of a multicomponent composite dosage form of the invention. The modified release dosage form embodiments are alternatively referred to in the art as controlled release, sustained release, extended release, delayed release, enteric release, pulsatile release, chronotherapeutic, time-dependent, pH-dependent, pH-independent, etc. All such prior art modified release technologies are considered adequate for use in the embodiments of the present invention as long as they are designed, and function, to release their contents from the stomach or proximal small intestine for absorption of a substantial amount of the dose in another portion, generally a more distal portion, of the GI tract.

Several mechanisms by which the dosage forms may be retained in the stomach are described in the prior art as well. These mechanisms are generally referred to as gastro-retentive delivery or gastric retention. Various mechanisms have been described to achieve gastro-retentive delivery all of which are suitable for the current invention. These mechanisms are described in "Gastroretentive Delivery Systems: A Mini Review" by Talukder and Fassihi, Drug Development and Industrial Pharmacy, Vol. 30, No. 10 pp. 1019-1028, 2004, and in the references cited previously by Chawla and by Hou, the disclosures of all three of which are hereby incorporated herein by reference in their entireties.

In order to deliver multiple "pulses" of active ingredient from the stomach, the product's dosage forms must comprise means for providing gastric retention of the dosage form and the means to provide the "pulses" of the active ingredient. The techniques available to the pharmaceutical formulator for such a dosage form are manifold, and it may assist purposes of discussion to break the type of "pulsing" from the stomach into four general types, the first type being a simple immediate release pulse, a second type may be characterized as having a lag time followed by rapid release, the third type being characterized as having a lag time followed by slow release, and a fourth type being characterized as a slow release pulse that does not have a substantial lag time.

Pulses of the First Type

Immediate release pulsing may be defined as any pulse, dosage form or part of a dosage form, which begins to dissolve upon delivery to a body cavity, preferably the oral cavity and the stomach in particular. Exposure to the liquid contents of the stomach will cause the pulse to begin releasing the active agent immediately. The release of the active agent from the immediate release pulse will be substantially free of any modified release characteristics designed to impart a lag time of more than about 15 minutes or to extend the release for more than about 45 minutes. Suitable immediate release dosage forms may be obtained from tablets, capsules, sachets, sprinkles, powders, beads, and other known delivery systems. Immediate release from tablets can be achieved by compressing an active agent with immediate release tabletting agents that are combined by commonly known processing techniques such as direct compression, roller compaction, slugging, wet low or high shear granulation, fluid bed granulation or others known to one skilled in the art. Immediate release from capsules may be obtained by several different methods. One method is to fill the capsule with powder, or with one or more immediate release tablets smaller than the diameter of the capsule, another is to produce a micro or multiparticulate pellet by methods known to one skilled in the art such as extrusion and spheronization; direct pelletization by rotor granulation or by the Glatt CPS technology; drug layering onto non-pariel or other cores, such as tablet cores; dry granulation; and micro-tabletting, such as is disclosed in U.S. patent application Ser. No. 11/277,831, filed Mar. 29, 2006, the disclosures of which are hereby incorporated by reference in their entireties. The products from the micro or multiparticulate methods above may also be filled into sachet packages for reconstitution into a solution or suspension or to be used as a sprinkle dosage form.

Immediate release ingredients suitable for use in the embodiments of the current invention are known to those of ordinary skill in the art, and such ingredients and processes can be found in multiple references, such as *Remington's Pharmaceutical Sciences*, 18$^{th}$ Ed., by Mack Publishing, Easton, Pa. (1995). The ingredients typically fall into the following non-limiting categories: 1) binders 2) diluents 3) disintegration aids 4) flow aids and 5) lubricants. Binders are necessary for creating cohesion between fine particles so that an acceptable granulation or tablet matrix may be formed. Non-limiting examples of suitable binders are polyvinylpyrollidone, hydroxypropylecellulose, hydroxypropylmethylcellulose, hydroxyethylcellulose, starch, maltodextrin, sucrose, and other binders. Diluents are needed to provide bulk to a formulation when the active agent dose and the quantity of other ingredients are too low to allow for adequate compression or granulation. Non-limiting examples of suitable diluents are lactose, mannitol, microcrystalline cellulose, calcium sulfate, calcium phosphate dihydrate, xylitol, maltodextrin, and other diluents. Disintegration aids may consist of the so-called disintegrants and may also consist of wetting agents, surfactants and other ingredients to aid dissolution of the active agent. Non-limiting examples of suitable disintegration aids are croscarmellose sodium, sodium starch glycolate, L-hydroxypropyl cellulose, sodium lauryl sulfate, polysorbate, macrogol glycerides, cyclodextrins, PEG-40-stearate, PEG-35 castor oil, PEG-20 glyceryl stearate, PEG-40 hydrogenated vegetable oil, PEG-6 corn oil, PEG-4 capyrilic/capric tryglicerides, PEG-8 caprylic/capric glycerides, Lauroyl macrogol-32 glycerides, stearoyl macrogol glyeride, PEG-6 apricot kernel oil, propylene glycol dicaprylate/dicaprate, propylene glycol diocanoate, propylene glycol caprylate/caprate, propylene glycol manolaurate, glyceryl monolinoliate, glyceryl caprylate, glyceryl caprylate/caprate, monoglycerides, PEG-20 sorbitan monolaurate, PEG-20 sorbitan monopalmitate, PEG-20 sorbitan monostearate, PEG-20 sorbitan monooleate, PEG-20 sorbitan monoisostearate, PEG-2 cetyl ether, PEG-20 cetyl ether, sucrose stearate, sucrose distearate, sorbitan monooleate, sorbitan monolaurate, sodium taurocholate, sodium deoxycholate, egg/soy lecithin, and other disintegration aids. Flow aids are incorporated when a blend of materials does not have sufficient flowability to achieve consistent fill weights on high speed tabletting or encapsulation machines. Non-limiting examples of suitable flow aids are colloidal silicon dioxide, talc, alkali stearates, and other flow aids. Lubricants are required to allow blends and granulations to perform on high speed tabletting and encapsulation machines without adhering to the metal surfaces during filling and compression stages where pressure is applied to the material. Non-limiting examples of suitable lubricants are sodium stearyl fumarate, magnesium stearate, calcium stearate, hydrogenated vegetable oil, polyethylene glycol, mineral oil, and other lubricants. In the case of the stearate salts non-bovine derived sources are preferred because of the concern over BSE contamination.

Pulses of the Second Type

Figure 1B:
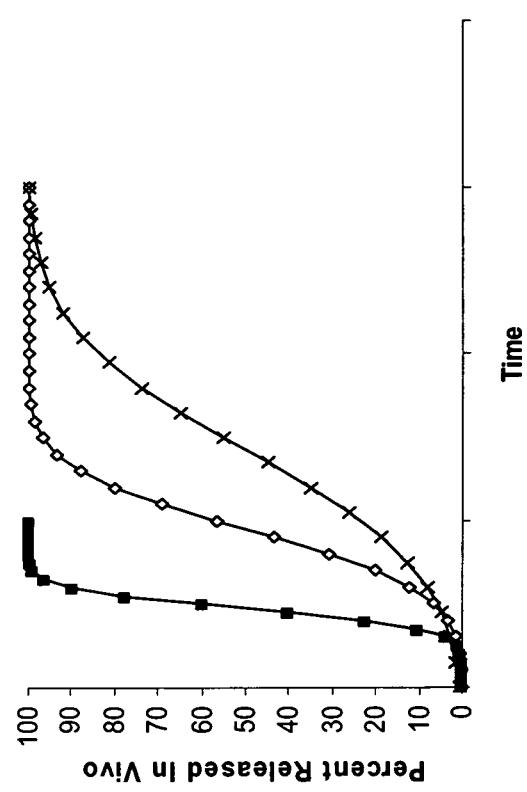
FIG. 1 is a graphical illustration of the pulse collapse effect.
Figure 2:
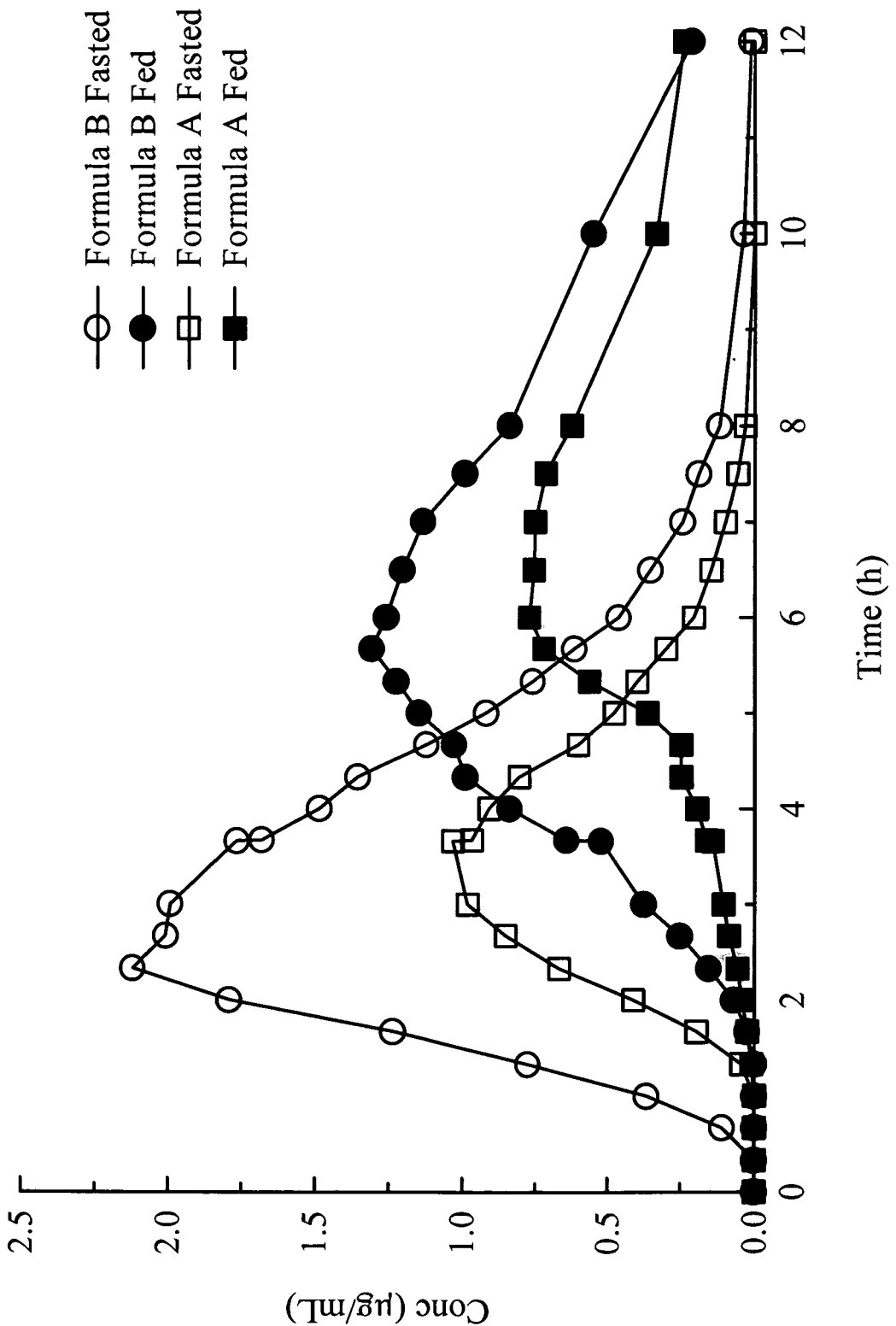
FIG. 2 represents the pharmacokinetic profile of two formulations, A and B, with trigger points of pH 7.5 and 6.8, respectively. The formulations were administered in the fed and fasted state. In both conditions the phenomenon of pellet spreading is evidenced by the reduced absorption rate of the higher trigger point formulation.
Figure 3:
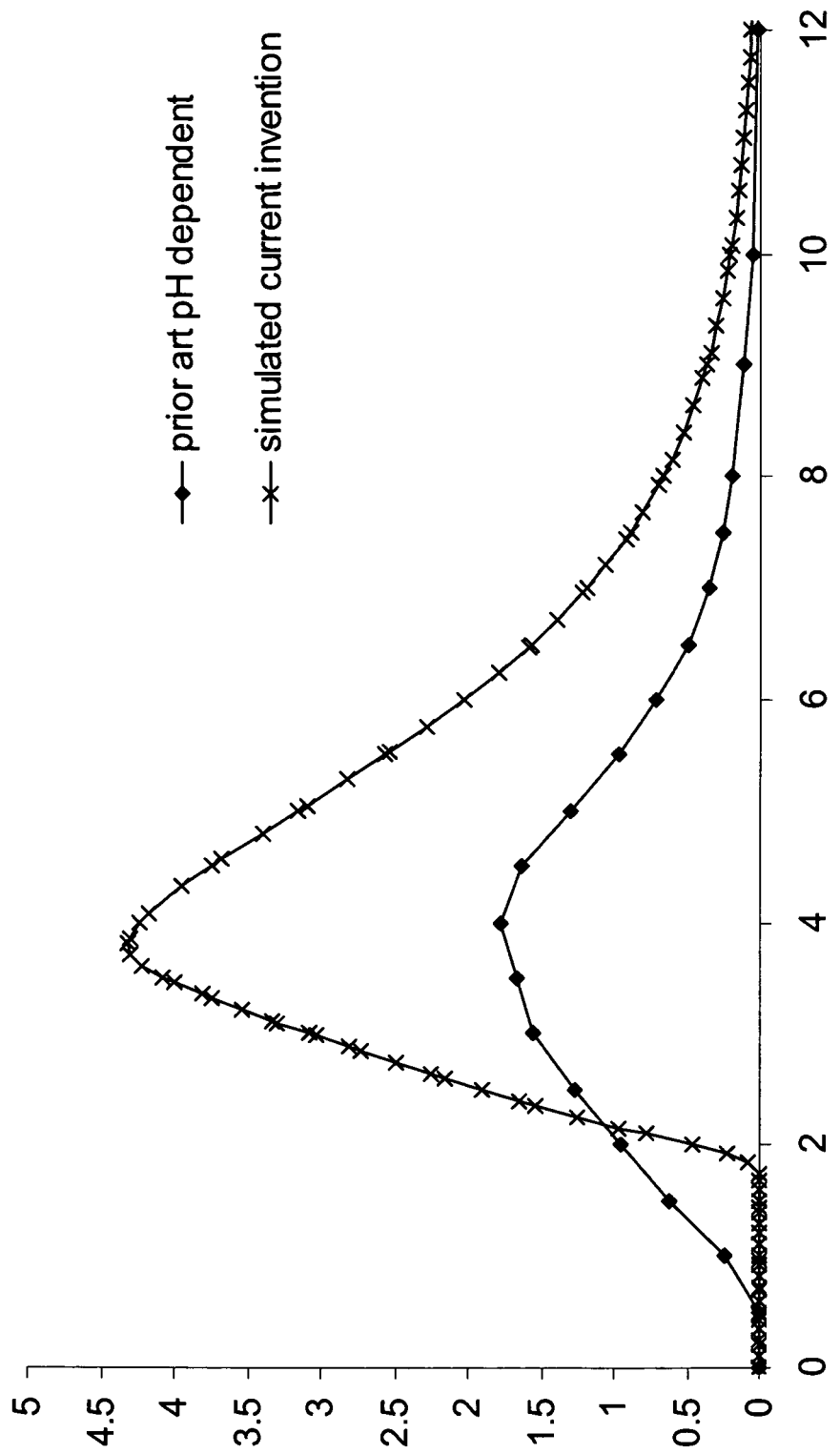
FIG. 3 is a graphical representation of actual pharmacokinetic performance of a prior art pH-dependent formulation with a pH trigger point of 7.5 versus a simulated pharmacokinetic profile of the current invention. Suggested from this graphic is the significantly improved lag time in the greatly increased bioavailability offered by the current invention.
Figure 4:
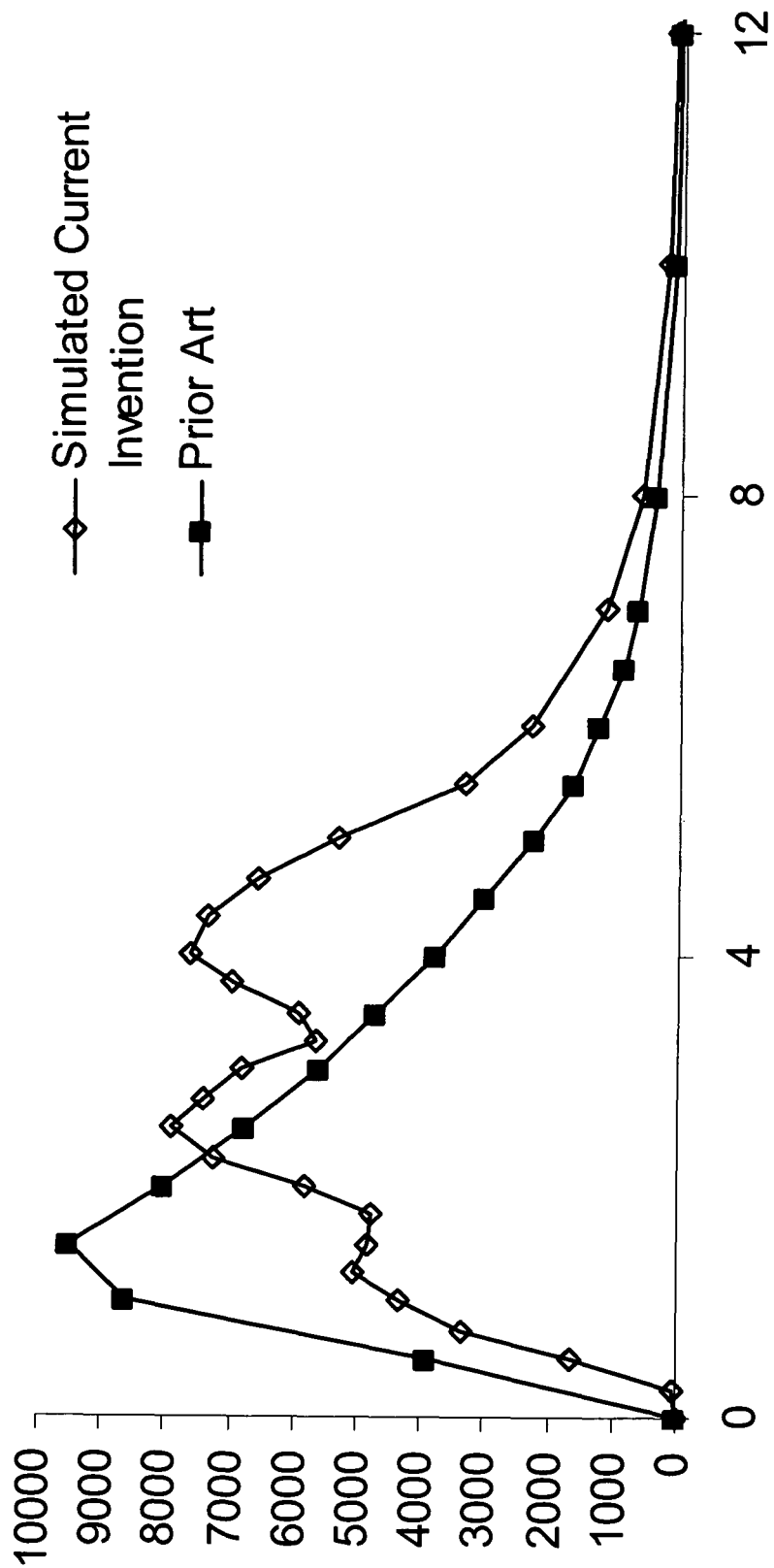
FIG. 4 graphically depicts the type of improvement possible from a composite three-pulse formulation. The prior art profile is actual pharmacokinetic data from a three-pulse product manufactured utilizing prior art technologies. The current invention profile is actual pharmacokinetic data generated by administering three equivalent immediate release doses at time zero, 1.5 hours and three hours; this type of dosing scheme represents the type of pharmacokinetic profile that can be made possible from a single dose of the current invention.

Pulses designed to provide a lag time followed by rapid release are commonly referred to in the art as delayed release. In the prior art the most common and successful example of this type of pulse is the enteric coated dosage form. Enteric coating provides a pH-dependent release from an acid insoluble coating such that no release occurs in the stomach, but upon exiting into the small intestine release is effected. The time and position of release in the body is controlled by the nature of the enteric polymer (i.e. the pH at which the polymer will dissolve and the thickness at which it is applied). A thicker polymer coating will take longer to dissolve and will release later than the same polymer film coated to a smaller dimension of thickness. The prior art enteric dosage form does not provide pulsing from the stomach, but rather must first exit the stomach to reach a pH that is high enough to dissolve the acid resistant polymer. The process of exiting the stomach causes the phenomena known as "pulse collapse," described graphically herein for the first time in FIG. 1.

In order to provide a delayed release pulse from the stomach a pH-independent or time-dependent mechanism is required. In addition to this requirement the pulse or dosage form or portion of the dosage form providing the pulse must be retained within the stomach, i.e. gastric retention is required, until the lag time and rapid subsequent release can be achieved. After initiation of the release the released drug is free to travel to more distal regions of the GI tract for absorption. Therefore it can be seen that without fulfilling both of these requirements, a) time-dependent release and b) gastric retention, a delayed release pulse which initiates from within the confines of the stomach cannot occur. Applicants believe that this has never been contemplated previously in the prior art.

Means to achieve pH-independent or time-dependent delayed release profiles are known to those skilled in the art, see *Pulsatile Drug Delivery Systems: A Review*, by Gothoskar, A V, Joshi, A M and Joshi, N H, Drug Delivery Technology, June 2004 Vol. 4 Number 5, the disclosures of which are hereby incorporated herein by reference in their entireties. These methods typically involve the use of a coating which: either dissolves or erodes over a certain time period; is subject to enzymatic, bacterial, chemical, or some other form of film degradation over time; or involves a type of swelling and rupturing coating system, typically a semipermeable film that allows liquid to penetrate into the core of the dosage form thus creating an internal pressure, either from osmosis or effervescence or swelling that results in the catastrophic failure of the film after a certain period of time. Examples of such methods utilizing acrylic polymers are described in EP 0436370 B1, and in U.S. Pat. No. 5,395,628 and U.S. Pat. No. 6,878,387, the disclosures of the latter two of which are hereby incorporated by reference in their entireties. Other systems may make use of a plug that does not allow release of the active agent until sufficient force is applied to the plug such that it is expelled. A critical aspect of the current invention, not contemplated by the prior art, is the need for such pH-independent or time-dependent systems to also be gastro-retentive.

The application of the coatings designed to achieve pH-independent systems for delayed release may be done through conventional coating technology, such as by use of a pan coater or by use of a fluid bed coater, electrostatic deposition, microencapsulation, spray drying, spray congealing or other spray or coating technique known to those skilled in the art. Preferred methods are solvent coating in a wurster column or pan coater. A more preferred method is the so-called dry coating process or core-in-core coating process, whereby a dry coating is applied to a core substrate by means of compression on a tablet press. Of the core-in-core tablet presses available those with a positive placement mechanism for placement of the inner core are regarded as better. Most preferred is an aqueous coating process in a fluid bed wurster column or coating pan.

In order to achieve a lag time followed by rapid release, a microparticulate wherein the particle size is less than about 1 mm may be used. A more preferred substrate would be a mini particle such as an extruded and spheronized core particle or a tablet of 1-6 mm in diameter. A plurality of these micro or mini particulates would then make up the desired dose. Most preferred is a large core particle such as a tablet of 7 mm in diameter or greater to allow for gastric retention by size exclusion means. For gastric retention by size exclusion tablets greater than 13 mm in diameter will be retained longer, and tablets greater than about 19 mm in their longest dimension will be retained for the longest time. Clinical scintigraphy studies conducted by Applicants utilizing standard pH-dependent enteric-coated tablets indicate that tablets greater than about 19 mm in their longest dimension will be retained in the stomach in the fed state for a minimum of 6 hours. A retention time of 6 hours would allow for the time spacing of initiation of 3 different pulses 3 hours apart (i.e. at time 0, 3 and 6 hours) or 4 different pulses 2 hours apart (i.e. at 0, 2, 4, 6). This represents a significant improvement over the prior art means to achieve pulsatile release by providing defined spacing between pulses from a single location above the window of absorption so that each pulse can be absorbed nearly as well as the first pulse. This will lead to later achievable Tmax, better overall bioavailability, and the optimum PK profile pulsatility.

For smaller particles that will not be retained in the stomach by size exclusion other methods for gastric retention will be required. These methods are described in the hereinabove-noted references, and consist of bioadhesion, density manipulation (i.e. floating dosage forms or high density dosage forms). A preferred method is to apply the bioadhesive as a coating to a suitable substrate which has a pH-independent or pH-dependent functional coating. Here it must be pointed out that a criticality for maintaining a rapid release is to use the bioadhesive in such a way that it will not substantially decrease the release rate for this second type of pulse.

Alternatively a pH-dependent coating may be used; in this case the bioadhesive coating functions to retain the enteric coated substrate within the stomach or the upper GI tract at a pH below the trigger point of the pH-dependent polymer, thus increasing the apparent lag time of the pulse. In the case of pH-dependent bioadhesive pulsatile systems the pH-dependent polymer may be the same for all pellets or it may be different. Where the pH-dependent polymer is identical for all pellets, separation of the pulse lag times is achieved by the quantity of bioadhesive, the type of bioadhesive, and the type of film former/binder utilized in the formation of the bioadhesive coating. Where the pH-dependent polymers are not identical (i.e. the pH-dependent polymers of each pulse dissolve at different pHs) bioadhesive coatings will extend the separation of pulse lag times achievable from plain, conventional, prior art pH-dependent pellets.

Various processing techniques may be utilized to produce the core for this second pulse type and they generally follow the same procedure as described for producing immediate release "pulses." A preferred method is wet granulation of active agent and binder followed by external addition of any swelling agents such as disintegrants that are required in the core. A more preferred method is a wet granulation technique with active binder and swelling agents that retain their swelling properties after a wetting and drying cycle such as croscarmellose sodium, starch paste, and L-HPC. For rapid release after a lag time the most preferred method for producing cores is a dry method such as direct compression, slugging, roller compaction, or organic solvent based granulation techniques that do not limit the type of swelling or disintegrating agent that may be used in the core.

Pulses of the Third Type

In cases where rapid release after the initial lag is not desired, the use of the disintegration agent may not be required. The same manufacturing techniques as described above for rapid releasing DR pulses may be used for delayed release pulses that exhibit a lag time followed by slow release. In place of the disintegration agent, sustained or controlled release agents may be substituted depending on the solubility of the drug or the dissolution properties of the core or the pH-independent methodology used. Suitable agents for slowing the release include hydrophilic polymers known to those skilled in the art, such as high molecular weight hydroxypropyl cellulose, high molecular weight hydroxypropyl methylcellulose, high molecular weight polyoxyethylene, starch, high molecular weight carboxyvinyl polymers, polyacrylic polymers, sucrose stearate, and other hydrophilic polymers particularly those with high molecular weight that gel or form a semipermeable film through which the active release rate is controlled by a form of diffusion kinetics. In many cases, and especially in the case of microparticulate or multiparticulate formulations containing active ingredients with good aqueous solubility, hydrophilic polymers will not retard the release sufficiently. In this case hydrophobic materials may be added to the core substrate to further slow the release rate. Exemplary hydrophobic materials are insoluble polymers such as ethylcellulose, cellulose acetate, and methacrylic polymers and copolymer systems. Other hydrophobic materials such as waxes or oily semisolids may also be used according to conventional methods known to those skilled in the art. Preferred hydrophobic waxes and semisolids include, but are not limited to glyceryl monooleate, glyceryl monostearate, glyceryl behenate, microcrystalline wax, carnauba wax, white bees wax, sucrose distearate, cetyl alcohol, glycerol dioleate, glycerol esters of fatty acids, glyceryl laurate, glyceryl palmitate, glyceryl monomyristate, stearic acid, and other hydrophobic waxes and semisolids.

Figure 7A:
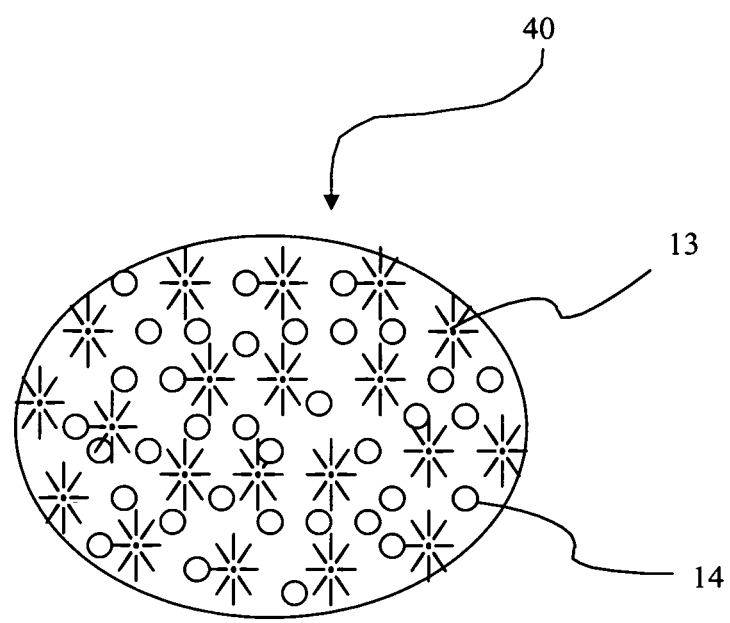
FIGS. 7(A) and 7(B) are illustrative cross sections of dosage forms designated generally by the reference numerals 40 and 50, respectively. Each shows the preferred methods of incorporation of the bioadhesive entities into the dosage form of the product of the instant invention.
Figure 7B:
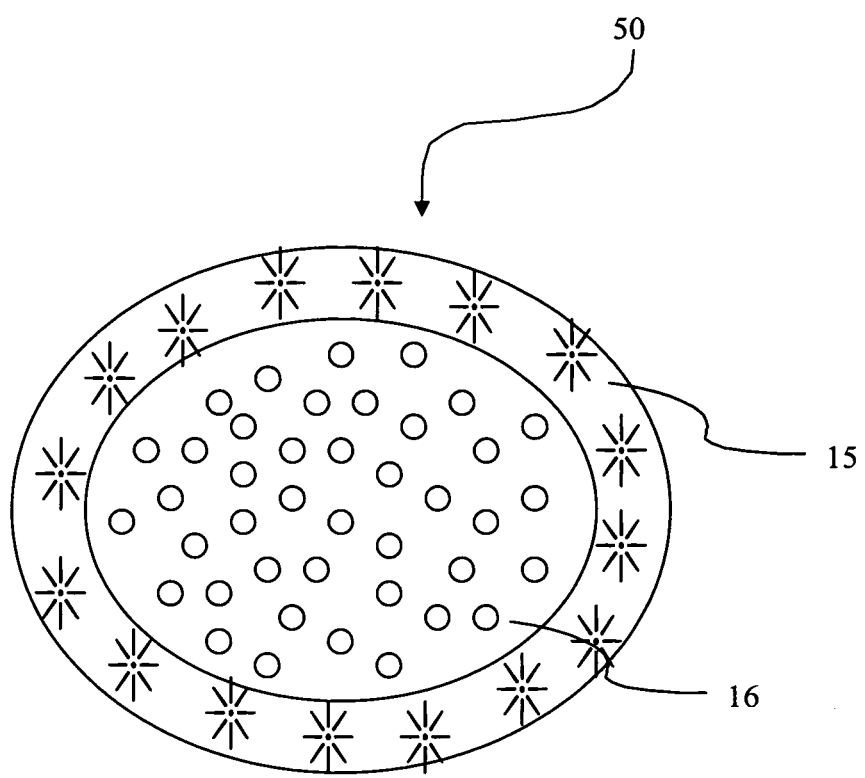
Figure 8:
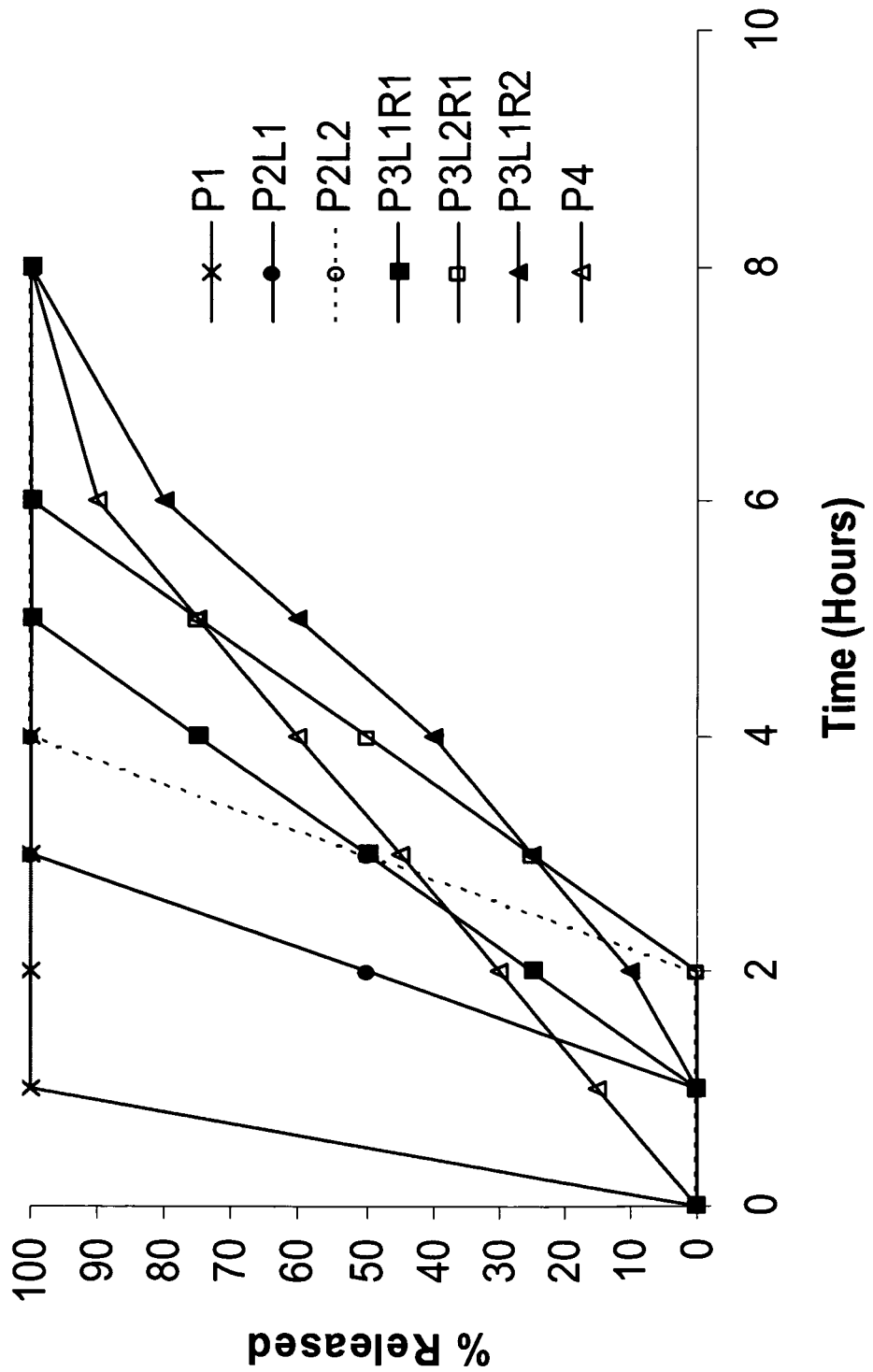
FIG. 8 illustrates some of the contemplated release profiles of the current invention.

The most preferred polymers or waxes for slowing the release of the active agent are those that also offer functionality as a bioadhesive, such as glycerol monooleate, sodium carboxymethylcellulose, polyacrylic acid, sodium alginate, polycarbophil, tragacanth, polyethylene oxide, methylcellulose, hydroxypropylmethylcellulose, polymethyl vinylether co-maleic anhydride, chitosan, and others known to one skilled in the art. In this manner the bioadhesive acts to slow the release of the active agent sufficiently while also providing the means to achieve gastric retention. This is especially useful in multiparticulate or microparticulate systems that do not have the benefit of gastric retention by size exclusion. The bioadhesive may be incorporated into the matrix of the core or may be applied to the outside of the core as a film coating as shown in FIGS. 7A and 7B, respectively, by the methods already described and known to those skilled in the art.

In a more preferred formulation the release rate after lag can be controlled purely by the design of the pH-independent mechanism. For instance, in the case where the pH-independent lag time is achieved by the use of a rupturable coating the extent to which the pH-independent coating ruptures will affect the release rate of the active agent out of the film, i.e. catastrophic failure can lead to rapid release while small tears or defects in the film can lead to a more controlled release rate. This is usually affected by controlling the ratio of soluble to insoluble film formers or additives. For instance, a film that contains a 1:1 ratio of hypromellose 2910 ethylcellulose 10 will release faster than a film with a ratio of 1:2 parts hypromellose 2910 ethylcellulose 10. This ratio, the thickness of the film, and the type of additives used in the film will also impact the release rate and the lag time.

In a preferred embodiment the pH-independent coating in combination with bioadhesive components acts in conjunction to slow the release. Either a pH-independent coating is applied to a core substrate that contains bioadhesive components or a bioadhesive coating is applied as a coating or layer on top of the pH-independent coating.

Osmotic dosage forms may also be suitable for use in the third pulse of the instant invention. Non-limiting examples of such dosage forms may be found in the disclosures of U.S. Pat. No. 4,765,989 and U.S. Pat. No. 4,327,725, which disclosures are hereby incorporated by reference in their entireties. These dosage forms may exhibit a lag time followed by sustained release, such as that illustrated in FIGS. 9 and 11 of U.S. Pat. No. 4,765,989. These patents contain examples of osmotic tablets that may be suitable as P3 type components in the instant invention, assuming their tablet dimensions are large enough to be retained in the stomach.

Pulses of the Fourth Type

The fourth type of pulsatile release envisioned in the current invention is a sustained release or controlled release pellet that releases at least about 50% of the active ingredient content from the stomach for absorption in the small intestine or colon.

As with the second and third type of "pulses" described above, two separate requirements must be met for this fourth type of "pulse." The first requirement is that the pulse must release from one area of the gastrointestinal tract for absorption in another part of the GI tract. Thus, gastric retention or upper enteral retention must be obtained. The second requirement for the fourth pulse is the sustained release characteristics. This fourth type of "pulse" does not have a lag time longer than about 15 minutes and generally takes longer than about one and a half hours for 80% of the active ingredient to be delivered. Preferably the lag time is less than about 10 minutes and the release is longer than about 4 hours. More preferably the lag time is less than about 5 minutes and the release is maintained for longer than about 6 hours.

For systems with a particle size larger than about 19 mm in the longest dimension the means to achieve gastric retention will largely be by a size exclusion mechanism of the pylorus. These dosage forms will usually be tablets or capsules that are rigid, non-eroding devices, or they may be swelling systems that gradually release the pharmaceutically active agent at the proscribed release rate. The dosage form will typically be administered in the fed state to enhance retention of the dosage form. As used herein, administering in the "fed state" means providing the dosage form in the time from between about 30 minutes prior to, and up to about 1, hour after a meal. Several methodologies to achieve this kind of size exclusion dosage form with a sustained release have been described in the prior art. It is believed that the utilization of this type of dosage form in conjunction with at least two of the other types of pulse systems described herein to produce a gastro-retentive release profile is not contemplated by the prior art. Preferred dosage forms larger than about 19 mm are conventional controlled release tablets or capsules that meet the requirements for gastric retention (i.e. sufficient size and rigidity of shape). Preferred dosage forms are those with coatings that can control the release rate sufficiently and can maintain the required rigidity under the forces of the GI tract, such dosage forms include the elementary osmotic systems or other osmotic or sustained release coated tablets that work by a diffusion rather than osmotic principle, meeting the release requirements of the fourth pulse outlined above.

These dosage forms are manufactured using controlled release techniques known to one skilled in the art, see *The Handbook of Pharmaceutical Controlled Release Technology*, edited by Wise, D L, 2000, Marcel Dekker, NY, except that they are designed to be of a certain minimum size and to maintain that minimum size for about 4 hours or more. Osmotic systems are generally manufactured by creating a core tablet containing the active pharmaceutical agent; and tabletting aids, especially any required solubility aids; and coating such core with a semipermeable membrane, such as cellulose acetate. Pores are then formed in the semipermeable membrane either by mechanical or laser drilling or by in situ methods by utilizing soluble pore forming ingredients incorporated into the semipermeable membrane. The pores allow for the osmotic pressure within the core of the tablet to be relieved by slowly "pumping" out the solubilized contents of the core in an effort to maintain equilibrium osmotic pressure. Diffusion membrane systems are similarly formed except that a semipermeable membrane is not utilized as the coating. Instead, a coating that is sufficiently permeable by the active pharmaceutical agent is utilized, and the release is controlled by diffusion of the active agent through the film coating in an effort to maintain reach concentration equilibrium on both sides of the film. As long as the osmotic or diffusion membrane maintains sufficient size and rigidity it will be retained in the stomach, releasing the pharmaceutical active agent for absorption in a more distal part of the GI tract.

Non-limiting examples of osmotic dosage forms suitable for use in the fourth pulse of the instant invention may be found in the disclosures of U.S. Pat. No. 6,110,498 and U.S. Pat. No. 6,838,093, which disclosures are hereby incorporated by reference in their entireties. These osmotic dosage forms will exhibit sustained release with minimal delay. Some dosage forms disclosed in U.S. Pat. No. 6,838,093 are specifically designed to mimic a $1^{st}$ order release profile, contrary to the more common zero order release profile commonly obtained with osmotic dosage forms. Dosage forms of this type, if manufactured in a large enough diameter or long axis dimension will be retained in the stomach and provide sustained release over a long period of time.

Dosage forms that will not be maintained in the stomach based on a size exclusion criteria (i.e. are smaller than about 19 mm) will need to rely on other methods to achieve gastric retention. (Several of those methods are described above). A preferred method of achieving gastric retention for smaller particles is by the use of high density materials to cause the dosage form to lodge in the folds and cavities of the stomach; a more preferred method is to utilize floating or buoyant dosage forms to achieve gastric retention. The most preferred method for achieving gastric retention when size exclusion methods are not available is bioadhesion.

For high density or low density floating pulse dosage forms standard methods described previously can be utilized to manufacture the dosage forms with the addition of the high density or floating materials to modify the density of the dosage form. High density dosage forms are achieved by addition of high density materials to the dosage form matrix. These materials include metals, metal oxides, and other high density materials designed to significantly increase the density of the dosage form. A drawback of this technique is the high amount of densifying materials required to make a significant increase in density. This limits the use of this technique to mainly low to moderate dose applications. Similar limitations apply to the floating type of dosage forms where extremely low density particles are manufactured with the intention of floating on the surface of the stomach contents. Floating can also be achieved with relatively low additional inactive ingredients when a chemical gas producing (effervescent) means is utilized. One drawback of the effervescent approach is that the processing and final dosage forms are sensitive to moisture, which can trigger the effervescent reaction prematurely.

Incorporation of bioadhesive agents into the dosage form was discussed previously. In the case of achieving sustained release without a lag time, bioadhesives provide dual purpose functionality. The bioadhesive agent provides the gastric retention for the dosage form and in many cases can also provide the sustained release properties required by this type of "pulse." Preferred bioadhesive materials have been disclosed above. Preferred means for incorporating bioadhesive materials were also disclosed above. In summary, the bioadhesive materials may be incorporated into the core matrix of the dosage form making up this "pulse," or they may be applied as a coating to the exterior of this pulse or one or more bioadhesive agents may be incorporated into both the core matrix and the exterior by coating.

In addition to bioadhesive agents, ingredients useful for the production of this "pulse" include controlled release agents such as the hydrophilic polymers and hydrophobic ingredients previously described and known to one skilled in the art. Other ingredients designed to enhance or retard the release as necessary to achieve clinical PK and PD goals may also be included. These may be solubility enhancers or permeability enhancers such as surfactants, fatty acids, fatty alcohols, glycerides, and combinations of such ingredients to form emulsions or microemulsion in situ.

Composite Dosage Form Design

Now that each of the four individual pulse types have been described it is beneficial to describe how a finished product might be designed to provide an improved pharmacokinetic pulsatile profile. The following non-limiting examples are intended to illustrate some of the ways that the current invention may be formulated into a finished product. It will be appreciated by one skilled in the art that there are infinite ways to combine the four different types of pulses, when each pulse can differ in lag time or release rate.

In general, each active pharmaceutical agent in the finished dosage form will have only one of the first and fourth type of pulse, but may contain multiple versions of the second and third type of pulse, since those pulses can both differ in lag time, providing essentially a new type of pulse within the general classification of the pulse. In addition, the third type of pulse may also differ in release rate after the lag time, providing even more options and flexibility in the design of the finished dosage form. In the case where more than one active pharmaceutical agent is delivered each agent may have one of the first and fourth type of pulse, and multiples of the second and third types. The pulses of each active pharmaceutical agent may be separate dosage forms, such as beads, pellets, powders, tablets, etc.; or the active agents may be combined into a single dosage form that releases both agents (i.e. a composite pulse). It is not required that both agents have the same lag time and release rate when released from a composite pulse; in fact solubility and permeability differences between active agents will likely lead to different release characteristics and absorption characteristics.

Prior to providing specific examples of the dosage forms envisioned by the inventors, it is useful to develop a nomenclature to describe the dosage forms and the possible pulsatile combinations. The envisioned pulse order can be explained by use of a pulsatile nomenclature, where pulses of the first type are referred to as $P_1$ and pulses of the second type are referred to as $P_{2L1}$, where L1 signifies a first lag time shorter than L2 and L2 is a shorter lag time than L3 etc.; pulses of the third type are denoted $P_{3L1R1}$, where L1 signifies a first lag time shorter than an L2 lag time, which is shorter than an L3 lag time and where R1 denotes a release rate faster than R2 which is faster than R3 etc.; and pulses of the fourth type are denoted $P_4$. For the second and third type of pulse the lag time notation will indicate where the lag time of each pulse type is in relation to the other pulse type. For instance, $P_{2L1}$ and $P_{3L1R1}$ would have the same lag time, $P_{2L2}$ and $P_{3L1R1}$ would indicate the second type of pulse has a longer lag time than the third type of pulse in the system. For pulses of the third and fourth types the release rate may be any of the type available to those skilled in the art, such rates are generally described as being zero or first order; Weibul; some combination or hybrid type of release profile, such as the so-called bi-phasic release patterns which can be a combination of immediate and sustained release profiles; or a combination of various order release rates. Release rate order for the nomenclature system is determined by the time to reach 80% dissolved by in vitro dissolution testing.

Then, a three-pulse system of the type $P_1P_{2L1}P_{2L2}$ would denote a three-pulse system with one immediate release pulse of the first type and 2 pulses of the second type each with a different lag time. By use of this nomenclature the following preferred pulsatile systems of the present invention can be delineated, but are not limited to: $P_1P_{2L1}P_{2L2}$, $P_1P_{2L1}P_{3L1R1}$, $P_1P_{2L1}P_{3L2R1}$, $P_1P_{2L1}P_4$, $P_1P_{3L1}R_1P_{3L2R1}$, $P_1P_{3L1R1}P_{3L1R2}$, $P_1P_3L_1R_1P_4$, $P_{2L1}P_{2L2}P_4$, $P_{2L1}$, $P_{3L1R1}$, $P_4$, $P_{2L1}P_{3L2R1}P_{3L1R2}$, $P_{3L1R1}P_{2L2}P_4$, $P_1P_{3L1R1}P_{2L2}$.

In order to create a finished dosage form that has three separate pulses the following design and methodologies have been contemplated by the inventors. For core units that will not be retained within the stomach by size exclusion the general procedure is to first manufacture the core of each pulse. In one embodiment the core of each pulse is identical and is a rapid release pulse. These cores meet the requirement for the first type of pulse, the immediate release pulse or $P_1$, and can be used in this capacity in the finished dosage form. To make the second pulse the cores are coated with a pH-independent coating polymer system as known in the art and previously described above. To this second pulse is added a bioadhesive coating layer as previously described. This bioadhesive layer is applied such that it can provide the desired gastric retention and at the same time not to slow the release rate of the pulse after the lag time. This second pulse gives a defined lag time and provides rapid release according to the requirements of the second type of pulse given above and may be denoted $P_{2L1}$. A third pulse is manufactured in a similar way to the second pulse except that the pH-independent coating that is applied creates a longer lag time than the second pulse in the dosage form. As with the second pulse a bioadhesive coating is applied in such a manner as to provide the necessary gastric retention and to allow for the release rate to meet the requirements of the second type of pulse. This pulse is then denoted in our nomenclature as $P_{2L2}$. In summary we have designed a dosage form of the type $P_1P_{2L1}P_{2L2}$, that has one immediate release pulse (type 1 pulse or IR pulse) and two delayed release pulses with rapid release after two different lag times (two of the second type of pulse described above) for a total of three separate pulses. It will be immediately recognized and contemplated that additional pulses can be added to the dosage form to effect even more pulsing.

Furthermore, it can be immediately recognized and contemplated that the two delayed pulses of the dosage form described above could be replaced in whole or in part by pulses of the third type described herein. There could then be an IR pulse followed by either one or two of either the second or third type of pulse described above, resulting in pulsatile dosage forms denoted in our nomenclature as: in the case of only one pulse of the third type—$P_1P_{2L1}P_{3L1R1}$ or $P_1P2_{L1}P_{3L2R1}$ or $P_1P2_{L2}P_{3L1R1}$ and in the case of two of the third type of pulse $P_1P_{3L1R1}P_{3L1R2}$ or $P_1P_{3L1R1}P_{3L2R1}$ or $P_1P_{3L1R1}P_{3L2R2}$. Alternately, the pulse of the first type or IR pulse may be removed and replaced with an additional pulse of the second, third, or fourth type. Furthermore, one of the pulses could be replaced by a pulse of the fourth type described above. For pulses of the third or fourth type the bioadhesive may be incorporated into the matrix of the core or may be applied as a coating to the exterior of the pulse as previously described.

In order to combine the individual pulse dosage forms into a single composite unit blending and filling technologies known to those skilled in the art are utilized. Preferred methodologies for blending are tumble or convection blending in blenders suitably sized for the batch weight being blended. Preferred blenders are V-blenders, slant-cone blenders, bin blenders, paddle mixers, or ribbon blenders manufactured by Patterson Kelly, LB Bohle, General Equipment Manufacturing Company (GEMCO), Hobart, Littleford Day, and others known to one skilled in the art. Blending times should be long enough to assure uniformity of the blend of pulses prior to filling into the finished dosage form. Once uniform blending is achieved the pulses can be filled into the finished dosage form. This may be a tablet, capsule, sachet, straw, ampule, bottle, vial, or other pharmaceutically acceptable receptacle or package design. Preferred filling equipment includes tablet presses appropriately sized to the size of the blend being tabletted. Common tablet manufacturers are Elizabeth-Hata, Korsch, IMA, SeJong, Kikusui, Fette, Stokes, Courtoy, Key, and others. Cores that are not of sufficient size for gastric retention will need to be further packaged into capsules, sachets, ampules, vials etc. Machinery is commonly available to the pharmaceutical industry to accomplish such filling. Not only can such machinery handle filling multiple capsules, but typically it can also handle filling multi or micro particulate formulations as well. Non-limiting examples of machinery and vendors available to provide such machinery are: the encapsulators and pouch fillers available from MG2, encapsulators and pouch fillers available from IMA, H&K capsule fillers available from Bosch, and pouch fillers available from Korber-MediPak. A preferred method of filling multi-pulse dosage forms is to avoid the requirement of blending by filling the individual pulse components on machinery that can handle multi-component fills. Preferred machinery is: MG2 Futura and Planeta encapsulators for up to 6 different pulses, IMA Zanasi encapsulators for up to three different pulses, pouch fillers by MG2, IMA, and Korber-Medipak for up to four or more different pulses.

Figure 5:
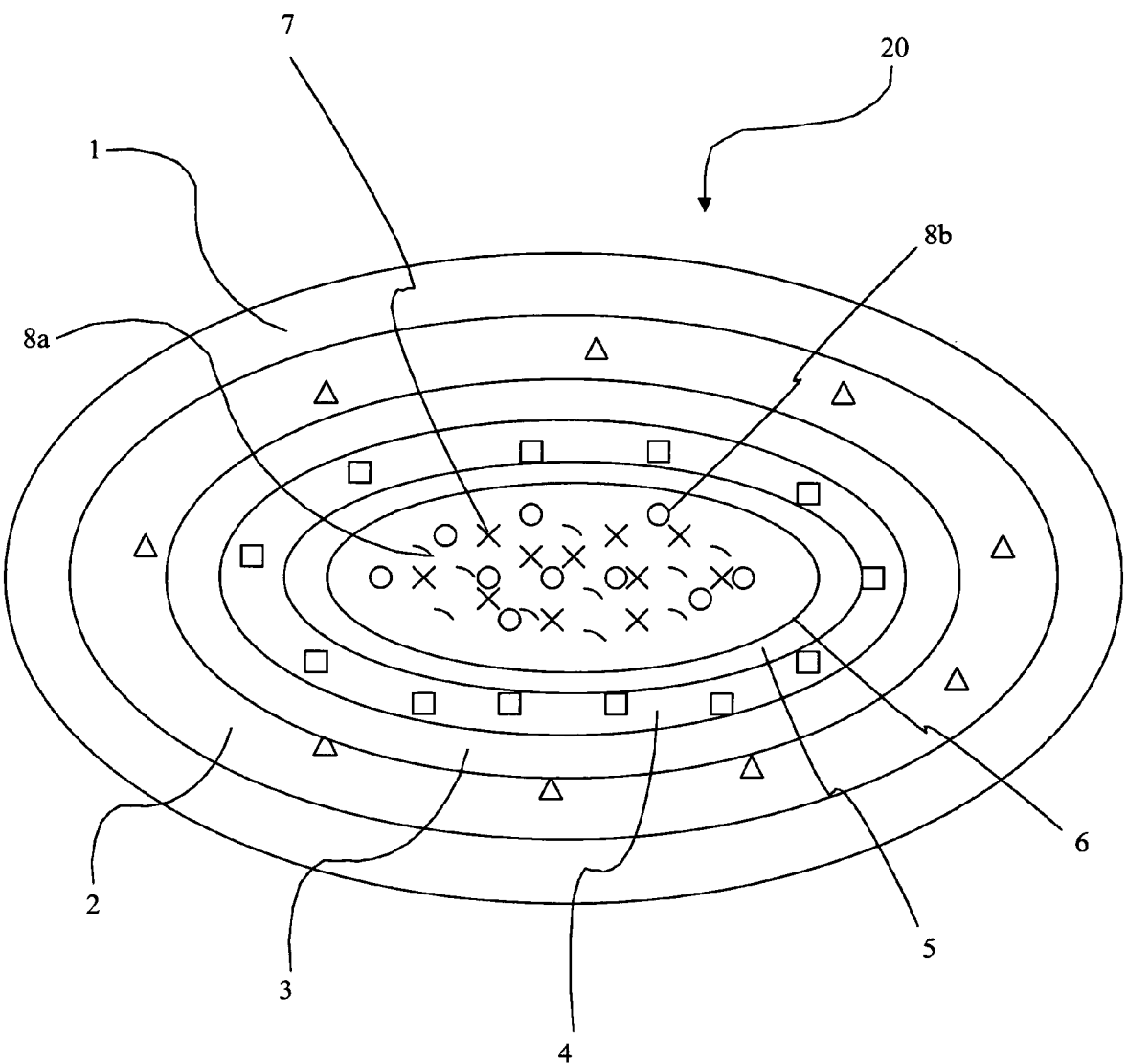
FIG. 5 is a cross section of a three-pulse composite tablet product of the current invention designated generally by the reference numeral 20. The three pulse composite tablet product includes an outer aesthetic/moisture barrier layer 1, that is non release rate modifying; an outermost drug layer 2, containing P1; a first pH independent layer 3 (providing a first delayed release); a drug layer 4 containing P2L1, which may be the same drug as in P1 or alternately may be a different drug, this drug layer may optionally contain a disintegrating agent to assist in the removal of the first pH independent layer 3; a second pH independent layer 5 (providing a second delayed release); an inner core tablet 6 containing drug for P2L2, which core tablet optionally contains any or each of: a disintegration agent 7 to assist with removal of coating, a hydrophilic bioadhesive agent 8a, or a hydrophobic bioadhesive agent 8b.
Figure 6:
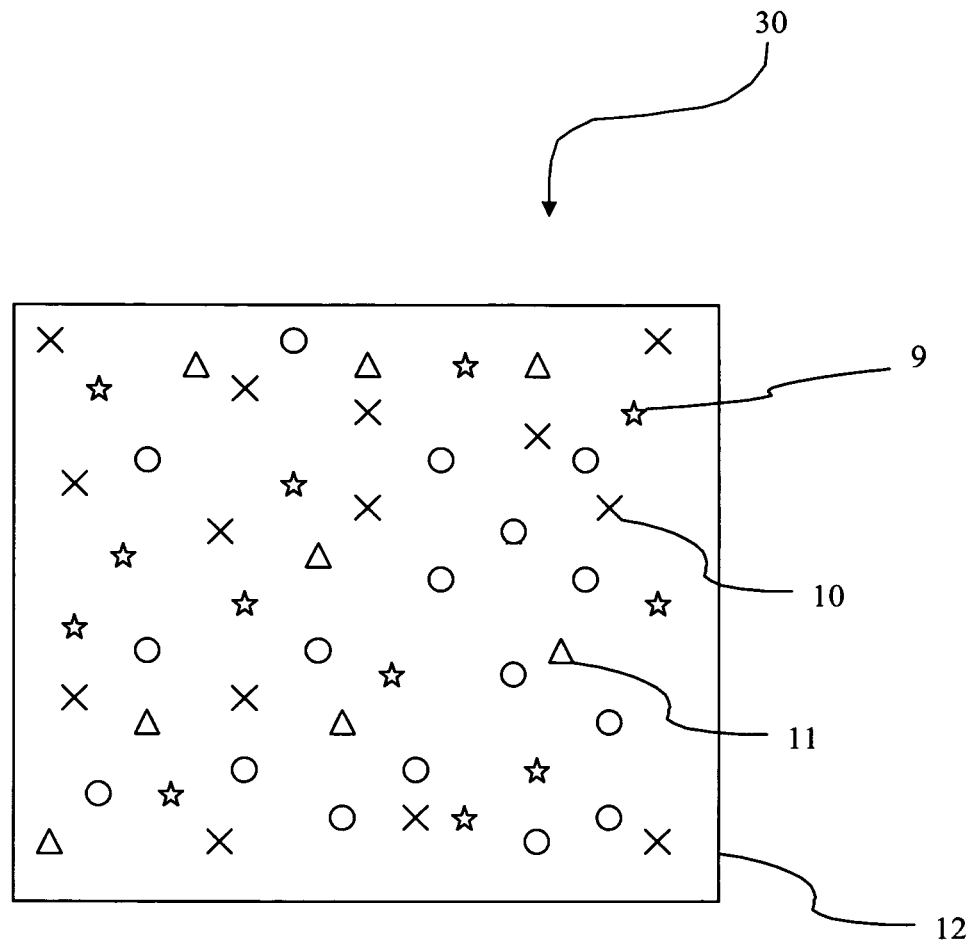
FIG. 6 is a cross section of a three-pulse composite pouch product of the current invention designated generally by the reference numeral 30. The three-pulse composite pouch product includes pellets 9, formulated for immediate release (P1); pellets 10, formulated for a first delayed release (P2L1); pellets 11, formulated for a delayed sustained release (P3L2); and a pouch or wall 12 to contain the pellets until administration as a sprinkle.

Now making use of the above-noted nomenclature when specifically considering finished dosage forms of the present invention that would be subject to gastric retention by size exclusion, the inventors envision the following: pulsatile dosage forms of the same nomenclatures as described above for non-size exclusion gastro-retentive dosage forms, where the dosage form consists of a large, rigid single unit with one dimension longer than 19 mm where the dosage form is administered with food. The preferred embodiment of the dosage form is a multiple layered tablet where the layers are applied by coating techniques known to those skilled in the art such as pan coating, fluid bed bottom spray or top spray coating, electro-deposition, solid coating by a core in core tabletting technique or other methods. The layers of the tablet dissolve from the outside of the dosage from in toward the center and provide the necessary pulses from each layer. In this manner the lag time of each successive inner layer of the dosage form must be equal to or later than the previous outer layer. Such a product is illustrated by FIG. 5.

In operation the dosage form would be administered to a patient in the fed state, and the tablet would be retained in the stomach. The outer layer of the tablet would begin to release immediately, $P_1$, alternately the first pulse may be excluded or it may be supplemented with a pulse of the fourth type, $P_4$. The first inner layer would then release a second pulse from the stomach of either the second or third type after some lag time L1. This first inner layer would then have the pulse nomenclature of $P_{2L1}$ or $P_{3L1R1}$ or $P_{3L1R2}$. The next most inner layer would then begin to release its contents from the stomach after another lag time L2. Using the nomenclature already established these pulses could be denoted as $P_{2L2}$ or $P_{3L2R1}$ or $P_{3L2R2}$. It will be appreciated that successive inner layer pulses can be added as long as gastric retention is maintained.

It is also envisioned by the inventors that any of the pulses, and especially the final pulse in the size exclusion tablet dosage form, may consist of pulses of the types described above in combination with a conventional pH-dependent pulse that may provide an added lag time longer than that achieved by existing pH-dependent dosage forms or even dosage forms of the current invention.

The size exclusion dosage form of the current invention is manufactured using conventional pharmaceutical process equipment and ingredients. First a core of the appropriate dimensions is prepared, preferably this will be an oblong or football shaped tablet with the long axis equal or greater than 19 mm. The core tablet is either an immediate release tablet or a sustained release core. Ingredients suitable for these purposes are described above. Alternatively the core tablet may contain bioadhesive entities in the matrix of the tablet or as a coating applied to the exterior of the core tablet. Furthermore, the core tablet may also contain additional pulses such as a pH-independent or pH-dependent pulse with or without bioadhesive. The core tablet is manufactured by standard pharmaceutical processing techniques using standard ingredients at levels accepted in the FDA Inactive Ingredient Database.

The steps for producing a tablet core are described in several good references, one being *Remington's Pharmaceutical Sciences*. In general there are 3 steps 1) producing a suitably flowable powder granulation of the constituent ingredients 2) adding necessary tabletting aids such as disintegrants and lubricants and 3) compressing the powder blend on a tablet press. There are many methods available to produce a flowable powder granulation including direct compression, wet or dry granulation, or slugging. A preferred method is wet high shear granulation with vertical granulators provided by vendors such as Niro, Glatt, Collette, Gral or Vector. A more preferred method is by dry granulation using roller compaction or slugging technique. The most preferred method is by direct compression using a tumble or paddle type mixer as described above. After a suitable blend of the active agent and other ingredients is made a final blend is typically required where the disintegration aid and tablet lubricant are added. This step is typically done in a tumble or paddle blender. The final blend is then compressed on a tablet press using tablet punches of the proper size and shape.

The core tablet is then coated with a pH-independent film coating. This coating is formulated to provide the desired lag time that may be longer or equivalent to the lag time of the next most outer pH-independent coating. The release rate from this coating may be either rapid release for a pulse of the second type or prolonged release for a pulse of the third type. Means to achieve different lag times and release rates are discussed above in the appropriate pulse section. The coating is applied in either a pan coater, a fluid bed coater, by electrodeposition, or by dry coating using a core in core tablet press. Suitable pan coater vendors are O'Hara Technologies, Thomas Engineering, Vector, Glatt, Driam, and others. For fluid bed coating a top or bottom spray technique may be used but bottom spray is more efficient, especially if using the HS Collar available from Glatt or the PrecisionCoater™ available from Niro, Vector, IMA, and O'Hara Technologies, among others also selling fluid bed coating equipment. Electro-deposition techniques are available from Phoqus and other specialty coating firms. Suitable core in core tablet press vendors are Korsch, IMA, Elizabeth Hata, Courtoy, and others.

Extending outward from the first pH-independent or time-dependent coating the next coating applied will likely be a layer of active agent to provide the next pulse. The active agent will be layered onto the exterior of the coated core described above. The layering will be by a coating mechanism similar to the methods used to apply the functional film coating onto the core tablet. Once this next layer of active agent is applied another layer of the functional pH-independent or time-dependent film coating is applied. It is applied in the same manner that the original film coating was applied. Next another layer of active agent is applied and the process of alternating active and functional coating continues until the desired number of pulses is attained.

The final exterior active agent coating may be an immediate, $P_1$, or a sustained release, $P_4$, type of coating. To achieve a sustained release type coating the active agent may be admixed with release controlling excipients and applied as a matrix type of coating or the active agent may be layered as an immediate release layer and a further functional release controlling coating may be applied of the active layer. Finally, it is understood that an aesthetic non-functional coating may be applied to mask the taste of the tablet or to impart a pharmaceutically elegant appearance to the tablet.

It will be immediately appreciated by those skilled in the art that the above described mode of pulsed dosing provides numerous advantages over the prior art. The advent of the current invention allows those pharmaceutically active agents that suffer from a limited window and a need to be delivered in multiple pulses of the kinds disclosed above to finally be delivered in a once-a-day or twice-a-day dosing regimen instead of the usual three to four times a day manner in which they are traditionally prescribed. Disease states that might benefit from such a form of delivery include microbial, viral, or fungal infection, asthma, arthritis, allergic rhinitis, peptic ulcer, gastroesophogeal reflux disease, hypercholesterolemia, cancer, epilepsy, attention deficit, hyperactivity, depression, sleep disorders, seasonal-affective disorder, diabetes and cardiovascular disease. Especially benefited by the current invention are those pharmaceutical agents with a narrow window of absorption so that they are not amenable to once or twice a day therapy. In addition, those pharmaceutical active agents that would benefit from a pulsatile or chronotherapeutic dosing regimen are particularly benefited by the ability of the current invention to provide such dosing regimens in a once-daily, or twice-daily, dose heretofore unobtainable and uncontemplated by the prior art.

The instant invention has application to pharmaceutical active agents known to have a limited window of absorption due to various absorption barriers, which could be biological or physico-chemical and, further, could be, but are not limited to poor solubility, low permeability, saturable active absorption, or influx mechanisms such as carrier mediated transport. In addition compounds that are converted to their active form via intestinal metabolism, such as some prodrugs, could also be beneficially administered by the invention hereinabove-described and hereinbelow-described. The instant invention has application to pharmaceutical active agents known to be substrates of active transporters or subject to a carrier mediated absorption process. The invention has application to all such substrates by initiating the release of the active agent above the window of absorption. One skilled in the art would appreciate that application insofar as many anti-infectives and other therapeutic agents have been determined to have a limited window of absorption. In a preferred embodiment the pharmaceutical active agent is a substrate for an active transport system. As non-limiting examples of the active transporters for which the pharmaceutical active agents of the present invention may act as substrates there may be mentioned PEPT1, PEPT2, large neutral amino acid transporter, organic cation transporter, monocarboxylic acid transporter, phosphate transporter, and other active transporters known to those of skill in the art. Preferred pharmaceutical active agents for the instant invention are those that are substrates for the PEPT1 and PEPT2 active transport systems. As non-limiting examples of such pharmaceutical active agents there may be mentioned the beta-lactam class of antibiotics, the beta-lactam subclasses (i.e., penicillins, cephalosporins, and carbapenems and their analogues), valacyclovir, certain ACE inhibitors, dipeptides, peptidomimetics, and other pharmacologically active agents that are known to those skilled in the art to be substrates for active transport systems or to have otherwise saturable absorption processes.

The invention may also have application to the following, non-limiting anti-infective drug classes: fluoroquinolones and their analogues, aminoglycosides and their analogues, macrolides/ketolides and their analogues, tetracyclines and their analogues, oxazolidinones and their analogues, and sulfonamides and their analogues. The following are further non-limiting examples of antibiotics useful in the present invention: cefadroxil, cefazolin, cefdinir, cephalexin, cephalothin, cephapirin, cefaclor, cefprozil, cephradine, cefamandole, cefonicid, ceforanide, cefuroxime, cefuroxime axetil, cefixime, cefoperazone, cefotaxime, cefpodoxime, cefpodoxime, proxetil, ceftazidime, ceftibuten, ceftizoxime, ceftriaxone, cefepime, cefmetazole, cefotetan, cefoxitin, loracarbef, imipenem, erythromycin (and erythromycin salts such as estolate, ethylsuccinate, gluceptate, lactobionate, stearate), azithromycin, clarithromycin, dirithromycin, troleandomycin, telithromycin, penicillin V, penicillin salts and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin), mezlocillin, piperacillin, piperacillin and tazobactam, ticarcillin, ticarcillin and clavulanate potassium, clindamycin, lincomycin, vancomycin, streptomycin, tobramycin, novobiocin, aminosalicylic acid, capreomycin, cycloserine, ethambutol HCl and other salts, ethionamide, isoniazid, ciprofloxacin, levofloxacin, lomefloxacin, nalidixic acid, norfloxacin, ofloxacin, sparfloxacin, moxifloxacin, moxifloxacin hydrochloride (and other salts of moxifloxacin), gatifloxacin, gemifloxacin, gemifloxacin mesylate (and other salts of gemifloxacin), sulfacytine, suflamerazine, sulfamethazine, sulfamethizole, sulfasalazine, sulfisoxazole, sulfapyrazine, sulfadiazine, sulfamethoxazole, sulfapyridine, linezolid, tetracycline, doxycycline, oxytetracycline, minocycline, demeclocycline, chlortetracycline, metronidazole, methenamine, fosfomycin, nitrofurantoin, trimethoprim, clofazimine, trimoxazole, pentamidine, tigecycline and trimetrexate.

The invention may also have application to the following, non-limiting protease inhibitor class of antivirals and their analogues: the nucleoside reverse trancriptase inhibitor (RTI) class of antivirals and their analogues, the non-nucleoside RTI class of antivirals and their analogues, the nucleotide RTI class of antivirals and their analogues, the viral cellular inhibitor class of antivirals and their analogues, the viral integrase inhibitor class of antivirals and their analogues, the inhibitors of viral/cell fusion and cell entry class of antivirals and their analogues, the DNA-polymerase inhibitor class of antivirals and their analogues, the DNA synthesis inhibitor class of antivirals and their analogues, the immunomodulator class of antivirals and their analogues, the viral nucleic acid release inhibitor class of antivirals and their analogues, the neuraminidase inhibitor class of antivirals and their analogues, the nucleoside analog antiviral class of antivirals and their analogues, the humanized monoclonal antibody class of antivirals and their analogues, neomycin, acyclovir, gancyclovir, cydofovir, amprenavir, fosamprenavir, atazanavir, saquinavir, indinavir, nelfinavir, abacavir, ritonavir, lopinavir, famciclovir, adefovir, emtricitabine, efavirenz, delavirdine, nevirapine, tenofovir, tenofovir disoproxil fumarate (and other salts and esters of tenofovir), oseltamivir, zanamavir, didanosine, foscamet, zidovudine, lamivudine, stavudine, hydroxyurea, enfuvirtide, T-20, T-1249, PRO-542, SCH-351125, S-1360, interferons, interferon-α2b, interferon-α2a, interferon-alfacon-1, flumantidine, amantidine, ribavirin, ribavirin and interferon-α2b, palivizumab, the azole class of antifungals, the azole subclasses, imidazoles, triazoles, and their analogues, the allylamine class of antifungals and their analogues, the polyene class of antifungals and their analogues, the echinocandin class of antifungals and their analogues, itraconazole, miconazole, clotrimazole, butoconazole, econozole, sulconazole, oxiconazole, tioconazole, bifonazole, croconazole, fenticonazole, isoconazole, omoconazole, terconazole, vibunazole, naftifine, butenafine, nystatin, natamycin, tolnaftate, haloprogin, undecylenic acid, chloroxylenol, ciclopirox, carbolfuchsin, clioquinol, methylrosaniline HCl, selenium sulfide, ketoconazole, fluconazole, itraconazole, voriconazole, posaconazole, caspofungin, anidulofungin, micafungin, terbinafine, amphotericin-b, flucytosine, griseofulvin, epirazolide.

The invention also has application to pharmaceutically active agents that exhibit a pH solubility profile whereby the solubility decreases with increasing pH, or agents that have a window of absorption due to low solubility or a slow dissolution rate. The absorption window time (or time available for absorption) of these agents can finally be sufficiently extended so as to allow for the development of effective controlled release systems. Non-limiting examples of such compounds are clarithromycin, ciprofloxacin, ketoconazole, atovaquone, and other BCS class II or IV compounds known to one skilled in the art.

Pharmaceutically active agents that exhibit a limited window of absorption due to permeability limitations such as low permeability or other saturable absorption processes will benefit by the invention. The invention provides a means for these compounds to be developed into effective controlled release delivery systems by releasing the active pharmaceutical agent from the dosage form above the critical window of absorption or segment of the GI tract that defines the window of absorption. Active agents that are highly charged in vivo and hence are mainly absorbed by the paracellular route are particularly suitable for the invention. Non-limiting examples of the agents are: quartemary ammonium compounds, neomycin, acyclovir, gancyclovir, itraconazole, epirazolide, doxycycline, ranitidine, cemitidine, and other BCS class III or IV compounds known to those skilled in the art.

In addition to pharmaceutically active agents that are only absorbed within a narrow window segment of the GI tract, compounds that have good or excellent absorption properties also are appropriate for use in the current invention, especially if said well absorbed compounds would benefit therapeutically from a more pulsatile pharmacokinetic profile or a profile that is not achieved by conventional controlled release formulation technology of the prior art. One area of pharmacotherapy that is gaining in importance is chronotherapy. Here the goal is to administer the pharmaceutical active agent when it is most beneficial to do so in the circadian rhythm of the host animal or in the cyclical pattern of the biological functioning or manifestation of the disease state. Disease states that exhibit this type of biological rhythm are known to those skilled in the art and include but are not limited to asthma, arthritis, attention deficit, hypercholesterolemia, cancer, cardiovascular disease, peptic ulcer disease, GERD, sleep disorder, depression, anxiety, and others.

Examples of active pharmaceutical agents useful in chronotherapy and other types of chemotherapy include the following non-limiting compounds grouped in general by class. Pharmaceutically active peptides and peptidomimetics include, but are not limited to TRH, DDAVP, LHRH agonists, LHRH antagonists, DADLE, metkephamid, oxytocin, insulin-like growth factors, growth hormone releasing factor, sleep inducing peptide, opiate antagonists, opiate agonists, DGAVP, somatostatin, peptide T, vasoactive intestinal polypeptide, gastric inhibitory peptide, cholecystokin and its active fragments, gastrin releasing peptide, ACTH and its analogues, enkephalins, aminopenicillins, cyclosporine, EPO, and others. Pharmaceutically active proteins include, but are not limited to, growth hormones, interferons, interleukins, calcitonin, insulin-like growth factors, insulin, colony stimulating factor, tumor inhibitory factors, transforming growth factors, epidermal growth factor, atrial naturetic factor, proinsulin, nerve growth factor, calcitonin, transforming growth factor beta, and glucagon. Other examples include the anti-inflammatory drugs such as phenylbutazone, indomethacin, naproxen, ibuprofen, flurbiprofen, diclofenac, dexamethasone, oxaprozin, prednisone and prednisolone; coronary dilator drugs such as glyceryl trinitrate, isosorbide dinitrate, and pentaerythritol tetranitrate; peripheral vasodilator drugs such as naftidrofuryl oxalate, cyclandelate, and nicotinic acid; psychotropic and/or an antianxiety drugs such as fluazepam, diazepam, amitryptaline, doxepine, thioridazine, trifluperazine, fluphenazine, piperothiazine, haloperidol, maprotiline hydrochloride, imipremine, clorazepate, estazolam, lorazepam, alprazolam, bupropion, fluoxetine, buspirone, clonazepam, sertaline, zolpidem, desmethylimipramine, lithium carbonate, lithium sulfate, and methylphenidate; central stimulant drugs such as isoproterinol, amphetamine sulphate, and amphetamine hydrochloride. Further examples may include antacids such as aluminum trisilicate, aluminum hydroxide, cimetidine, ranitidine, famotidine, omeprazole, and nizatidine; gastrointestinal sedatives such as propantheline bromide and metoclorpramide; cerebral vasodilators such as soloctidilum, naftidrofuryl oxalate, co-dergocrine mesylate, papaverine, and pentoxifylline; anti-anginal drugs such as amyl nitrate, isosorbide dinitrate, pentaerythritol tetranitrate, verapamil, nifedipine, diltiazem, and glyceryl trinitrate; cardiac inotropic agents such as digoxin, medigoxin, digitoxin, amrinone, and lanatoside C; antiarrythmics such as verapamil, nifedipine, diltiazem, disopyramide, bretylium tosylate, quinidine sulfate, quinidine gluconate, and procainamide; antihypertensives such as methyldopa, eprosartan, losartan, irbesartan, reserpine, valsartan, telmisartan, hydralazine, propranolol, labetalol, sotalol, terazosin, enalapril, lisinopril, quinalapril, benazepril, ramipril, clonidine, fosinopril, felodipine, immodipine and amlodipine; vasoconstrictors such as ergotamine; substances which influence blood coagulability such as protamine sulfate and epsilon aminocaproic acid; hypnotics such as dichloral phenazone, nitrazepam, and temazepam; antinauseants such as chlorpromazine and promethazine theoclate; anticonvulsants such as sodium valproate, phenyloin sodium, divalproex sodium, and carbamazepine; neuromuscular drugs such as dentrolene sodium; hypoglycemic agents such as diabenese, insulin, glyburide, glipizide, and troglitazone; appetite suppressants such as asphenteramine, diethylproprion hydrochloride, and fenfluramine hydrochloride; erythropoietic substances such as folic acid, calcium gluconate, and ferrous sulphate; antiasthmatic drugs such as aminophylline, theophylline, orciprenaline sulphate, terbutaline sulphate, albuterol and salbutamolanticholesterol agents such as lovastatin, gemfibrozil, simvastatin, and pravastatin; beta-blockers such as such as acebutolol, alprenolol, atenolol, labetalol, metoprolol, nadolol, oxprenolol, pindolol and propranolol; anti-neoplastic agents and immunosuppressants, such as aminoglutethimide, amsacrine, azathioprine, bicalutamide, bisantrene, busulfan, camptothecin, cytarabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, and toremifene citrate. In addition to the foregoing active ingredient examples the instant invention further contemplates the use of pharmaceutically acceptable salts thereof and combinations thereof.

It should be further appreciated that the dosage forms described above may further consist of more than one active agent, and the different active agents may be incorporated into the dosage form as any type of pulse. The different active agents may be released together in the same pulsatile pattern or individual pulse profiles may be created for each active according to the pharmacokinetic needs of the active agent.

Now the invention will be described by way of examples that disclose how each of the four-pulse types might be manufactured and how the four-pulse types might be combined into a single dosage form to yield a finished product with a multi-pulse profile.

EXAMPLES

Example A-1

Metro Pellets ($P_1$)

A dosage form for the pulse one ($P_1$) delivery of metronidazole was prepared as follows: 15 g of Cremophor EL, 60 g of Povidone K25, 50 g of sucrose and 75 g of corn starch were dispersed in 800 g of water (20% solids) and heated to 80-85° C. for 5 minutes. A uniform paste was formed and allowed to cool to room temperature. The resultant paste was granulated with 500 g of micronized metronidazole, 140 g of Avicel PH101, and 160 g of L-HPC. The granulation was extruded through a 0.8 mm screen and spheronized into pellets. The pellets were dried in an oven at 50° C. until the moisture content determined by loss on drying (LOD) was less than 3%. Pellets passing through a 16 mesh screen and retained on a 30 mesh screen were collected with the following composition:

| COMPONENT | WT % |
|---|---|
| Metronidazole, micronized | 50.0% |
| Avicel PH101 | 14.0% |
| L-HPC (LH-BB1) | 16.0% |
| Sucrose | 5.0% |
| Povidone, K25 | 6.0% |
| Cremophor EL | 1.5% |
| Corn Starch | 7.5% |
| Total | 100.0% |

Example A-2

Metro Pellets ($P_{2L1}$)

Pellets from Example A-1 were coated with two functional layers in order to achieve a lag time followed by quick release of drug. A "push" layer that swells when hydrated was applied to the pellets to help rupture the outer coating in order to achieve the quick release of drug once the lag time has passed. PVP and Ac-Di-Sol were dispersed in Isopropanol and sprayed onto 500 g of pellets to a 40% solids weight gain using a bottom spray fluid bed coater with an inlet temperature of 50° C. and parameters sufficient to maintain an exhaust temperature around 40° C. After the "push" layer, a layer was applied to protect the inner drug core from dissolving for a set period of time. Ethocel, Methocel, Talc, Cabosil and TEC were dispersed in a hydro-alcoholic solution and the functional layer was applied to 500 g of pellets at a 40% solids weight gain using a bottom spray fluid bed coater with an inlet temperature of 60° C. and parameters sufficient to maintain an exhaust temperature around 45° C. The coating solution compositions are as follows:

| COMPONENT | WT % | G/Batch |
|---|---|---|
| Push layer | | |
| Substrate (pellets) | n/a | 500.0 |
| Ac-Di-Sol | 12.0% | 150.0 |
| Kollidon 90 | 4.0% | 50.0 |
| Isopropanol | 84.0% | 1050.0 |
| pH Independent Layer | | |
| Substrate (pellets) | n/a | 500.0 |
| Ethocel Std 10 | 3.57% | 119.0 |
| Methocel E5P LV | 1.53% | 51.0 |
| Altalc 500 | 0.57% | 19.0 |
| Cab-O-Sil M5P | 0.03% | 1.0 |
| Triethyl Citrate | 0.30% | 10.0 |
| Ethanol | 84.60% | 2820.0 |
| Water | 9.40% | 313.3 |

Example A-3

Metro Pellets ($P_{3L2R1}$)

Pellets from Example A-1 were coated with three functional layers in order to achieve gastric retention for a period of time followed by quick release of drug once the pellets empty from the stomach. A "push" layer that swells when hydrated was applied to the pellets to help rupture the outer coating in order to achieve the quick release of drug once the pellets leave the stomach. HPC and Ac-Di-Sol were dispersed in isopropanol and sprayed onto 500 g of pellets to a 40% solids weight gain using a bottom spray fluid bed coater. After the "push" layer, an enteric polymer layer was applied to protect the inner drug core from dissolving in the stomach. An Eudragit L30D-55 dispersion was prepared with TEC and Talc and the enteric layer was applied to 500 g of pellets at a 20% solids weight gain using a bottom spray fluid bed coater. After the enteric layer a mucoadhesive layer was applied in order to achieve dose form retention in the stomach. A dispersion of Ethocel, Polyox and GMO in Ethanol was prepared and the mucoadhesive layer was applied to 500 g of pellets at a 20% solids weight gain using a bottom spray fluid bed coater. The coating solution compositions are as follows:

| COMPONENT | WT % | G/Batch |
|---|---|---|
| Push layer | | |
| Substrate (pellets) | n/a | 500.0 |
| Ac-Di-Sol | 12.0% | 150.0 |
| HPC-EF | 4.0% | 50.0 |
| Isopropanol | 84.0% | 1050.0 |
| Enteric Layer | | |
| Substrate (pellets) | n/a | 500.0 |
| Eudragit L30D-55 | 58.7% | 241.46 |
| TEC | 2.2% | 9.05 |
| Talc | 4.5% | 18.51 |
| Water | 34.6% | 142.33 |
| Mucoadhesive Layer | | |
| Substrate (pellets) | n/a | 500.0 |
| Ethocel 10 | 5.1% | 22.2 |
| PEO N301 | 15.3% | 66.7 |
| GMO | 2.6% | 11.1 |
| Ethanol | 77.0% | 334.8 |

Example A-4

Metro Capsules ($P_1P_{2L1}P_{3L2R1}$)

Capsules were prepared for the controlled delivery of Metronidazole in order to achieve a first pulse quick release of drug followed by a second pulse quick release of drug after a lag time followed by a third pulse sustained release after a lag time. Pellets from Examples A-1, A-2 and A-3 were filled into capsules according to the following composition:

| COMPONENT | Metronidazole Content (mg) | MG/DOSAGE FORM |
|---|---|---|
| Metronidazole Pellets ($P_1$) (Example A-1) | 50 | 100 |
| Metronidazole Pellets ($P_{2L1}$) (Example A-2) | 50 | 392 |
| Metronidazole Pellets ($P_{3L2R1}$) (Example A-3) | 50 | 392 |
| Total | 150 | 884 |

Example B-1

Amox Pellets ($P_1$)

A dosage form for the pulse one ($P_1$) delivery of Amoxicillin was prepared as follows: A granulating solution was prepared containing 136.5 g of water, 6.5 g of Polyoxyl 35 Castor Oil, and 13.0 g of Povidone K30. 598.0 g of Amoxicillin Trihydrate was blended with 32.5 g of Microcrystalline Cellulose in a high shear mixer and then wet granulated by adding the granulating solution while mixing. The wet granulation was extruded using a dome granulator. The elongated extrudate was spheronized into rounded pellets using a marumerizer and then dried in a fluid bed dryer. The resulting pellets were sized using a 20, 30, and 40 mesh screen. The pellets retained on the 30 and 40 mesh screens were collected and contained the following composition:

| COMPONENT | WT % |
|---|---|
| Amoxicillin Trihydrate Powder, USP | 92.0% |
| Avicel PH101 | 5.0% |

| COMPONENT | WT % |
|---|---|
| Kollidon K30 | 2.0% |
| Cremophor EL | 1.0% |
| Total | 100.0% |

Example B2

Amox Pellets ($P_{2L1}$)

Pellets from Example B-1 were coated with a pH-dependent functional layer in order to achieve a quick release of drug once the pellets empty from the stomach where the pH of the GI tract is greater than 5.5. An enteric polymer layer was applied to protect the inner drug core from dissolving in the stomach. An Eudragit L30D-55 dispersion was prepared with TEC and Talc and the enteric layer was applied to 500 g of pellets at a 20% solids weight gain using a bottom spray fluid bed coater. The coating solution composition is as follows:

| COMPONENT | WT % | G/Batch |
|---|---|---|
| Enteric Layer | | |
| Substrate (pellets) | n/a | 500.0 |
| Eudragit L30D-55 | 58.7% | 241.46 |
| TEC | 2.2% | 9.05 |
| Talc | 4.5% | 18.51 |
| Water | 34.6% | 142.33 |

Example B-3

Amox Pellets ($P_{2L2}$)

Pellets from Example B-1 were coated with a pH-dependent functional layer in order to achieve a quick release of drug once the pellets empty from the stomach where the pH of the GI tract is greater than 6.5. An enteric polymer layer was applied to protect the inner drug core from dissolving in the stomach. An Aqoat dispersion was prepared with TEC, Talc and SLS and the enteric layer was applied to 500 g of pellets at a 30% solids weight gain using a bottom spray fluid bed coater. The coating solution composition is as follows:

| COMPONENT | WT % | G/Batch |
|---|---|---|
| Enteric Layer | | |
| Substrate (pellets) | n/a | 500.0 |
| AQOAT AS-HF | 6.8% | 89.8 |
| SLS | 0.2% | 2.7 |
| Talc | 2.0% | 27.0 |
| TEC | 2.3% | 30.6 |
| Water | 88.7% | 1179.5 |

Example B-4

Amox Pellets ($P_{3L1R1}$)

Pellets from Example B-2 were coated with a mucoadhesive layer in order to achieve dose form retention in the upper GI tract followed by controlled release once the dosage form reaches the target pH. A mucoadhesive coating dispersion was prepared by mixing Ethanol and Eudragit L100 with an overhead mixer until Eudragit was dissolved. Polyox was sieved through a 200 mesh screen and added it to the Ethanol/Eudragit RL100 solution. The resulting dispersion was sprayed onto 800 g of pellets to a 25% solids weight gain using a bottom spray fluid bed coater. After the mucoadhesive layer was applied, a 12% Opadry dispersion in water was prepared and sprayed onto 800 g of pellets to a 10% solids weight gain using a bottom spray fluid bed coater. The pellets were sieve cut using 18 and 40 mesh screens. Pellets retained on the 40 mesh screen were collected. The coating solutions compositions are as follows:

| COMPONENT | WT % | G/Batch |
|---|---|---|
| Mucoadhesive Layer | | |
| Substrate (pellets) | n/a | 800.0 |
| Eudragit RL100 | 8.0% | 48.2 |
| Polyox WSR301 SFP | 24.0% | 144.6 |
| Glyceryl Monooleate | 1.2% | 7.2 |
| Ethanol | 66.8% | 402.4 |
| Topcoat | | |
| Substrate (pellets) | n/a | 800.0 |
| Opadry Blue | 12.0% | 80 |
| Water | 88.0% | 586.7 |

Example B-5

Amox Pellets ($P_{4R2}$)

A dosage form for the controlled delivery of Amoxicillin was prepared as follows: first, 2,000 g of Amoxcillin Trihydrate, compacted grade was blended together with 1,520 g of Polyox WSR 301, 400 g of Manucol and 80 g of Magnesium Stearate in a V-blender. The blend was compressed into tablets and then sized using a Fitzmill to produce granules. The granules were sieve cut using 14 and 20 mesh screens. The granules retained on the 20 mesh screen were collected having the following composition:

| COMPONENT | WT % |
|---|---|
| Amoxicillin Trihydrate, compacted grade | 50.00% |
| Polyox WSR 301 SFP | 38.00% |
| Manucol F MCLF | 10% |
| Magnesium Stearate | 2.00% |
| Total | 100.0% |

Example B-6

Amox Tablet ($P_1P_{2L2}P_{4R1}$)

A large tablet dosage form for the controlled delivery of Amoxicillin was prepared in order to achieve a first pulse quick release of drug followed by a second pulse sustained release of drug followed by a third pulse release of drug after a lag time. 532.1 g of Pellets from Example B-3, 919.2 g of pellets from Example B-5 and 344.8 g of Amoxicillin Trihydrate compacted grade were blended together with 638 g of SMCC 90, 106.4 g of PVP, 79.8 g of Ac-Di-Sol and 39.9 g of Magnesium Stearate in a V-blender. The blend was compressed into 10 mm oval tablets with the following composition:

| COMPONENT | WT % | MG/DOSAGE FORM |
|---|---|---|
| Amoxicillin Trihydrate Compacted | 14.7% | 172.4 |
| Amoxicillin Trihydrate ($P_{4R1}$) Pellets (Example B-5) | 39.3% | 459.8 |
| Amoxicillin Trihydrate ($P_{2L2}$) Pellets (Example B-3) | 20.0% | 234.3 |
| SMCC 90 | 17.5% | 205.3 |
| Kollidon K30 | 4.0% | 46.9 |
| Ac-Di-Sol | 3.0% | 35.1 |
| Mag Stearate | 1.5% | 17.6 |
| Total | 100.0% | 1171.3 |

Example B-7

Amox Tablet ($P_{2L1}P_{2L2}P_{4R1}$)

A large tablet dosage form for the controlled delivery of Amoxicillin was prepared in order to achieve a first pulse quick release of drug after a lag time and second pulse sustained release of drug after a lag time followed by a third pulse release of drug after a lag time. The tablets of Example B-6 were coated with the pH-Independent polymer layer of Example C-2 having the following composition:

| COMPONENT | WT % | G/Batch |
|---|---|---|
| pH-Independent Layer | | |
| Substrate (tablets) | n/a | 800.0 |
| Ethocel Std 10 | 2.6% | 66.0 |
| Methocel E5P LV | 1.6% | 42.0 |
| Triethyl Citrate | 0.5% | 12.0 |
| 90% Ethanol | 72.7% | 1880.0 |
| Water | 22.7% | 586.7 |

Example B-8

Amox Tablet ($P_1P_{2L1}P_{2L2}P_{4R1}$)

A large tablet dosage form for the controlled delivery of Amoxicillin was prepared in order to achieve a first pulse quick release of drug followed by a second quick release of drug after a lag time and third pulse sustained release of drug after a lag time followed by a fourth pulse quick release of drug after a lag time. Tablets from Example B-7 were coated with an Active layer containing Amoxicillin. The coating method of Example C-3 was used to apply the 52.9% solids weight gain Amoxicillin Active layer. The coating compositions are as follows:

| COMPONENT | WT % | G/Batch |
|---|---|---|
| Active Layer | | |
| Substrate (tablets) | n/a | 800.0 |
| Amoxicillin Trihydrate milled powder | 23.9% | 388.0 |
| HPMC E5 | 2.2% | 34.9 |
| Water | 73.90% | 1198.9 |
| Topcoat | | |
| Substrate (tablets) | n/a | 800.0 |
| Opadry Blue | 12.0% | 80 |
| Water | 88.0% | 586.7 |

Example B-9

Amox Tablet ($P_1P_{2L1}P_{3L1R1}$)

A large tablet dosage form for the controlled delivery of Amoxicillin was prepared in order to achieve a first pulse quick release of drug followed by a second pulse quick release of drug after a lag time and third pulse sustained release of after a lag time. 449.6 g of Pellets from Example B-2, 824.3 g of pellets from Example B-4 and 344.8 g of Amoxicillin Trihydrate compacted grade were blended together with 438.2 g of SMCC 90, 89.9 g of PVP, 67.4 g of Ac-Di-Sol and 33.7 g of Magnesium Stearate in a V-blender. The blend was compressed into 10 mm oval tablets with the following composition:

| COMPONENT | WT % | MG/DOSAGE FORM |
|---|---|---|
| Amoxicillin Trihydrate Compacted | 15.3% | 172.4 |
| Amoxicillin Trihydrate ($P_{3L1R1}$) Pellets (Example B-4) | 36.7% | 412.1 |
| Amoxicillin Trihydrate ($P_{2L1}$) Pellets (Example B-2) | 20.0% | 224.8 |
| SMCC 90 | 19.5% | 219.1 |
| Kollidon K30 | 4.0% | 45.0 |
| Ac-Di-Sol | 3.0% | 33.7 |
| Mag Stearate | 1.5% | 16.9 |
| Total | 100.0% | 1123.9 |

Example B-10

Amox Tablet ($P_1P_{3L1R1}P_{4R2}$)

A large tablet dosage form for the controlled delivery of Amoxicillin was prepared in order to achieve a first pulse quick release of drug followed by a second pulse sustained release of drug after a lag time and third pulse sustained release of drug. 689.7 g of Pellets from Example B-5, 824.3 g of pellets from Example B-4 and 344.8 g of Amoxicillin Trihydrate compacted grade were blended together with 665.4 g of SMCC 90, 110.3 g of PVP, 82.8 g of Ac-Di-Sol and 41.4 g of Magnesium Stearate in a V-blender. The blend was compressed into 10 mm oval tablets with the following composition:

| COMPONENT | WT % | MG/DOSAGE FORM |
|---|---|---|
| Amoxicillin Trihydrate Compacted | 12.5% | 172.4 |
| Amoxicillin Trihydrate ($P_{3L1R1}$) Pellets (Example B-4) | 29.9% | 412.1 |
| Amoxicillin Trihydrate ($P_{4R2}$) Pellets (Example B-5) | 25.0% | 344.8 |
| SMCC 90 | 24.1% | 332.7 |
| Kollidon K30 | 4.0% | 55.2 |
| Ac-Di-Sol | 3.0% | 41.4 |
| Mag Stearate | 1.5% | 20.7 |
| Total | 100.0% | 1379.3 |

Example B-11

Amox Capsule ($P_{3L1R1}P_{2L2}P_{4R2}$)

A composite pellet dosage form for the controlled delivery of Amoxicillin was prepared in order to achieve a first pulse sustained release of drug at a specific rate of release after a lag time followed by a second pulse quick release of drug after a lag time and third pulse sustained release of drug. For each composite dose 257.7 mg of pellets from Example B-3, 340.0 mg of pellets from Example B-4 and 379.3 mg of pellets from Example B-5 were filled into 00el capsules.

Example C-1

Ceph Tablets ($P_1$)

A dosage form for the pulse one delivery of Cephalexin was prepared as follows: first, 162 g of Hypromellose 2910, USP (Methocel E5 Premium LV) was dissolved in purified water at 10% weight by weight. 5,250 g of Cephalexin powder, USP was charged to a mixer granulator and the Hypromellose solution was gradually added while mixing. The wet granulation was discharged and sized using a mill. The milled wet granulation was then dried at 65° C. for 3 hours and sized again using a mill. Next, the dried and milled granulation was passed through a 900 □m screen. 4,512 g of the Cephalexin granulation was subsequently dry blended with 250 g of Crospovidone and 200 g of ProSolv SMCC 90 for 8 minutes. 35 g of Magnesium Stearate was added to the dry blend and blended for an additional 2 minutes. The final blend was compressed into 10 mm oval tablets containing the following composition:

| COMPONENT | WT % | MG/DOSAGE FORM |
|---|---|---|
| Cephalexin, USP | 87.6% | 530.22 |
| Hypromellose 2910, USP (Methocel E5 Premium LV) | 2.7% | 16.34 |
| Silicified Microcrystalline Cellulose (Prosolv SMCC 90) | 4.0% | 24.21 |
| Crospovidone, NF (Polyplasdone XL) | 5.0% | 30.26 |
| Magnesium Stearate, NF | 0.7% | 4.24 |
| Purified Water, USP | 0.0%[a] | [a] |
| Total | 100.0% | 605.28 |

[a]Water removed during processing

Example C-2

Ceph Tablets ($P_{2L1}$)

Tablets from Example C-1 were coated with a pH-Independent polymer system in order to have a quick release of drug after a set amount of time. A pH-Independent polymer dispersion was prepared by mixing Ethocel, Methocel, and TEC in 90% Ethanol. The pH-Independent layer was applied to 800 g of tablets at a 15% solids weight gain using a pan coater. The coating solution composition is as follows:

| COMPONENT | WT % | G/Batch |
|---|---|---|
| pH-Independent Layer | | |
| Substrate (tablets) | n/a | 800.0 |
| Ethocel Std 10 | 2.6% | 66.0 |
| Methocel E5P LV | 1.6% | 42.0 |
| Triethyl Citrate | 0.5% | 12.0 |
| 90% Ethanol | 72.7% | 1880.0 |
| Water | 22.7% | 586.7 |

Example C-3

Ceph Tablets ($P_1P_{2L1}$)

Tablets from Example C-2 were coated with a polymer system containing Cephalexin in order to achieve a quick release of drug followed by a specified lag time and then a second quick release of drug. A polymer dispersion was prepared containing Cephalexin. HPMC was dissolved in water and micronized Cephalexin was dispersed in the polymer solution. The Active layer was applied to 800 g of tablets at a 49% solids weight gain using a pan coater. After the Active layer, an Opadry coating was applied from a 12% solution using a pan coater. The coating solutions compositions are as follows:

| COMPONENT | WT % | G/Batch |
|---|---|---|
| Active Layer | | |
| Substrate (tablets) | n/a | 800.0 |
| Cephalexin, micronized | 23.9% | 358.7[a] |
| HPMC E5 | 2.2% | 32.3 |
| Water | 73.9% | 1108.4 |
| Topcoat | | |
| Substrate (tablets) | n/a | 800.0 |
| Opadry Blue | 12.0% | 80 |
| Water | 88.0% | 586.7 |

[a]Pulse dose equals 100 mg/tablet.

Example C-4

Ceph Tablets ($P_1P_{2L1}P_{2L2}$)

Tablets from Example C-3 were coated with a pH-Independent polymer layer and with an Active layer in order to achieve a first pulse quick release of drug followed by a specified lag time followed by a second quick release of drug followed by a specified lag time followed by a third quick release of drug. The coating method of Example C-2 was applied to the substrate (Example J) followed by application of the coating method of Example C-3.

Example C-5

Ceph Tablets ($P_1$)

The granulation, blend and compression method of Example C-1 was used to make small round tablets to fill composite tablet doses into capsules. The final blend was compressed into 7 mm round tablets containing the following composition:

| COMPONENT | WT % | MG/DOSAGE FORM |
|---|---|---|
| Cephalexin, USP | 87.6% | 180.36 |
| Hypromellose 2910, USP (Methocel E5 Premium LV) | 2.7% | 5.58 |
| Silicified Microcrystalline Cellulose (Prosolv SMCC 90) | 4.0% | 8.24 |
| Crospovidone, NF (Polyplasdone XL) | 5.0% | 10.3 |
| Magnesium Stearate, NF | 0.7% | 1.52 |
| Purified Water, USP | 0.0%[a] | [a] |
| Total | 100.0% | 206 |

[a]Water removed during processing

Example C-6

Ceph Tablets ($P_{2L1}$)

Tablets from Example C-5 were coated with the pH-Independent polymer system of Example C-2 in order to have a quick release of drug after a set amount of time. The pH-Independent layer was applied to 800 g of tablets at a 15% solids weight gain using a pan coater.

Example C-7

Ceph Tablets ($P_{2L2}$)

Tablets from Example C-5 were coated with the pH-Independent polymer system of Example C-2 in order to have a quick release of drug after a set amount of time. The pH-Independent layer was applied to 800 g of tablets at a 30% solids weight gain using a pan coater.

Example C-8

Ceph Tablets ($P_{3L1R2}$)

Tablets from Example C-6 were coated with a mucoadhesive layer in order to achieve dose form retention in the upper GI tract followed by controlled release after a lag time. A mucoadhesive coating dispersion was prepared by dispersing Klucel, Carbopol and Triacetin in Ethanol. The dispersion was sprayed onto 800 g of tablets to a 20% solids weight gain using a pan coater. After the mucoadhesive layer was applied, a 12% Opadry dispersion in water was prepared and sprayed onto 800 g of tablets to a 2.5% solids weight gain using a pan coater. The coating solutions compositions are as follows:

| COMPONENT | WT % | G/Batch |
|---|---|---|
| Mucoadhesive Layer | | |
| Substrate (tablets) | n/a | 800.0 |
| Klucel EFX | 6.0% | 9.6 |
| Triacetin | 0.5% | 0.8 |
| Carbopol 971P | 3.5% | 5.6 |
| Ethanol | 90.0% | 144.0 |
| Topcoat | | |
| Substrate (tablets) | n/a | 800.0 |
| Opadry White | 12.0% | 80 |
| Water | 88.0% | 586.7 |

Example C-9

Ceph Tablets ($P_{3L2R1}$)

Tablets from Example C-7 were coated with a mucoadhesive layer in order to achieve dose form retention in the upper GI tract followed by controlled release after a lag time. The mucoadhesive coating dispersion of Example C-8 was sprayed onto 800 g of tablets to a 10% solids weight gain using a pan coater. After the mucoadhesive layer was applied, a 12% Opadry dispersion in water was prepared and sprayed onto 800 g of tablets to a 2.5% solids weight gain using a pan coater.

Example C-10

Ceph Tablets ($P_{3L2R2}$)

Tablets from Example C-7 were coated with a mucoadhesive layer in order to achieve dose form retention in the upper GI tract followed by controlled release after a lag time. The mucoadhesive coating dispersion of Example C-8 was sprayed onto 800 g of tablets to a 20% solids weight gain using a pan coater. After the mucoadhesive layer was applied, a 12% Opadry dispersion in water was prepared and sprayed onto 800 g of tablets to a 2.5% solids weight gain using a pan coater.

Example C-11

Ceph Tablets ($P_{3L1R1}$)

Tablets from Example C-6 were coated with a mucoadhesive layer in order to achieve dose form retention in the upper GI tract followed by controlled release after a lag time. A mucoadhesive coating dispersion was prepared by dispersing Klucel, Carbopol and Triacetin in Ethanol. The dispersion was sprayed onto 800 g of tablets to a 10% solids weight gain using a pan coater. After the mucoadhesive layer was applied, a 12% Opadry dispersion in water was prepared and sprayed onto 800 g of tablets to a 2.5% solids weight gain using a pan coater. The coating solutions compositions are as follows:

Example C-12

Ceph Capsules ($P_{2L1}P_{3L2R1}P_{3L1R2}$)

A composite dose form was prepared for the controlled delivery of Cephalexin such that a first pulse quick release of drug occurs after a lag time along with a second pulse sustained release of drug at a specific rate of release after the lag time followed by a third pulse sustained release of drug at a specific rate of release after a lag time. Tablets from Examples C-6, C-8 and C-9 were filled one each into 00el capsules.

Example C-13

Ceph Capsules ($P_1P_{3L1R1}P_{3L2R1}$)

A composite dose form was prepared for the controlled delivery of Cephalexin such that there is a first pulse quick release of drug followed by a second pulse sustained release of drug at a specific rate of release after a lag time followed by a third pulse sustained release of drug at the same rate of release after a lag time. Tablets from Examples C-5, C-11 and C-9 were filled one each into 00el capsules.

Example C-14

Ceph Capsules ($P_1P_{3L1R1}P_{3L1R2}$)

A composite dose form was prepared for the controlled delivery of Cephalexin such that there is a first pulse quick release of drug followed by a second pulse sustained release of drug at a specific rate of release after a lag time along with a third pulse sustained release of drug at a specific rate of release. Tablets from Examples C-5, C-11 and C-8 were filled one each into 00el capsules.

Example C-14

Ceph Capsules ($P_1P_{3L1R1}P_{2L2}$)

A composite dose form was prepared for the controlled delivery of Cephalexin such that there is a first pulse quick release of drug followed by a second pulse sustained release of drug at a specific rate of release after a lag time followed by a third pulse quick release of drug after a lag time. Tablets from Examples C-5, C-11 and C-7 were filled one each into 00el capsules.

The invention claimed is:

1. An oral pharmaceutical product for providing at least three pulses of at least one antibiotic to a patient, said at least three pulses being released from said product from a first location in the patient's gastrointestinal tract, wherein said first location in the patient's gastrointestinal tract is the stomach, for absorption thereof at a second location in the patient's gastrointestinal tract, said second location being different from said first location and being more distal in the gastrointestinal tract than said first location, said second location in the patient's gastrointestinal tract being selected from the group consisting of the duodenum, the jejunum, the ileum, the colon, and combinations of the foregoing, said product comprising:
   first, second, and third pharmaceutical dosage forms; each of said pharmaceutical dosage forms comprising at least one antibiotic and a pharmaceutically acceptable carrier, wherein the at least second pharmaceutical dosage form comprises at least one of a bioadhesive coating, a high density material, a floating material or a diameter of 7 mm or greater,
   wherein the at least third pharmaceutical dosage form comprises at least one of a bioadhesive coating, a high density material, a floating material or a diameter of 7 mm or greater;
   wherein said 7 mm diameter, said bioadhesive coating, said high density material and/or said floating material provide temporary gastric retention within said first location in the patient's gastrointestinal tract via size exclusion, bioadhesion or density manipulation;
   wherein each of said first, second, and third pharmaceutical dosage forms have different lag times,
   wherein the first pharmaceutical dosage form is an immediate release dosage form, the second pharmaceutical dosage form is a delayed release dosage form comprising a pH-independent release mechanism, and wherein said delayed release dosage form exhibits a lag time followed by rapid release of the at least one antibiotic, wherein the third dosage form is a sustained release dosage form, and
   wherein the at least one antibiotic of said third dosage form is released after the at least one antibiotic of the second dosage form and wherein 100% of the at least one antibiotic of the second dosage form is released within one hour of initiation of release.

2. The pharmaceutical product of claim 1, wherein the oral product is selected form the group consisting of tablets, capsules, sachets, sprinkles, ampules, solutions, and multiple units thereof.

3. The pharmaceutical product of claim 1, wherein the release of said pulse of at least one antibiotic from each of said pharmaceutical dosage forms is separated by at least one hour.

4. The pharmaceutical product of claim 1, wherein said pulse of at least one antibiotic from each of said pharmaceutical dosage forms is about at least 50% dissolved before release of said pulse of at least one antibiotic is initiated from the subsequently releasing dosage form.

5. The pharmaceutical product of claim 1, wherein the release of said pulse of at least one antibiotic from each of said pharmaceutical dosage forms is separated by about at least one hour and wherein said pulse of at least one antibiotic from each of said pharmaceutical dosage forms is about at least 50% dissolved before release of said pulse of at least one antibiotic is initiated from the subsequently releasing dosage form.

6. The pharmaceutical product of claim 1, wherein the pulses are released so that the corresponding $C_{max}$ of each of the at least three pulses is distinguishable in a pharmacokinetic plasma profile.

7. The pharmaceutical product of claim 1, wherein the pulses are released so that the corresponding $T_{max}$ of each of the at least three pulses is distinguishable in a pharmacokinetic plasma profile.

8. The pharmaceutical product of claim 1, wherein the corresponding $C_{max}$ and $T_{max}$ of each of the at least three pulses is distinguishable in a pharmacokinetic plasma profile.

9. The pharmaceutical product of claim 1, wherein the antibiotic is selected from metronidazole, cephalexin and amoxicillin.

* * * * *